United States Patent
Wende et al.

(10) Patent No.: US 10,088,469 B2
(45) Date of Patent: Oct. 2, 2018

(54) METHOD FOR OBTAINING BLOOD PLASMA FROM A WHOLE BLOOD SAMPLE

(71) Applicant: QIAGEN GmbH, Hilden (DE)

(72) Inventors: Andy Wende, Hilden (DE); Sabine Werner, Hilden (DE); Ralf Himmelreich, Mainz (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 14/423,527

(22) PCT Filed: Aug. 29, 2013

(86) PCT No.: PCT/EP2013/067886
§ 371 (c)(1),
(2) Date: Feb. 24, 2015

(87) PCT Pub. No.: WO2014/033208
PCT Pub. Date: Mar. 6, 2014

(65) Prior Publication Data
US 2015/0204843 A1      Jul. 23, 2015

(30) Foreign Application Priority Data

Aug. 30, 2012  (EP) .................................... 12182333

(51) Int. Cl.
| | |
|---|---|
| *G01N 33/49* | (2006.01) |
| *C12N 15/10* | (2006.01) |
| *C12Q 1/68* | (2018.01) |
| *C12Q 1/6806* | (2018.01) |

(52) U.S. Cl.
CPC ....... *G01N 33/491* (2013.01); *C12N 15/1003* (2013.01); *C12Q 1/6806* (2013.01)

(58) Field of Classification Search
None
See application file for complete search history.

(56) References Cited

U.S. PATENT DOCUMENTS

| | | |
|---|---|---|
| 3,552,928 A | 1/1971 | Fetter et al. |
| 5,076,950 A | 12/1991 | Ullman et al. |
| 5,118,428 A | 6/1992 | Sand et al. |
| 5,136,095 A | 8/1992 | Tarnowski et al. |
| 5,282,982 A | 2/1994 | Wells |
| 5,482,829 A | 1/1996 | Kass et al. |
| 5,609,771 A | 3/1997 | Pelmulder |
| 5,876,605 A | 3/1999 | Kitajima et al. |
| 6,403,384 B1 | 6/2002 | Lea |
| 7,754,499 B2 | 7/2010 | Poirier et al. |
| 2004/0157219 A1* | 8/2004 | Lou .................... C12N 15/1013 435/6.11 |

FOREIGN PATENT DOCUMENTS

| | | | | |
|---|---|---|---|---|
| CA | 1338603 C | * | 9/1996 | ......... G01N 33/5094 |
| EP | 1995316 A1 | * | 11/2008 | ......... C12N 15/1006 |
| WO | 02/29406 A1 | | 4/2002 | |
| WO | WO 0229406 A1 | * | 4/2002 | ............... B03C 1/01 |
| WO | 2010/003493 A1 | | 1/2010 | |
| WO | 2012/038503 A1 | | 3/2012 | |

OTHER PUBLICATIONS

Shasby et al. "Active transendothelial transport of albumin. Interstitium to lumen", Circulation Research 57(6): 903-908, 1985.*
Andreou et al. (EP 1995316 A1, EPO machine translation).*

* cited by examiner

*Primary Examiner* — Emily A Cordas
(74) *Attorney, Agent, or Firm* — Seed IP Law Group LLP

(57) ABSTRACT

A method for obtaining blood plasma from a whole blood sample comprising the following steps a) contacting the whole blood sample with a composition (A) comprising at least one carboxylic acid, wherein the addition of the acidic composition (A) and optionally further additives to the whole blood sample provides a sample mixture having a pH that lies in a range from 2.5 to 5; b) binding red and white blood cells to a magnetic solid phase; wherein step a) and step b) can be performed sequentially or simultaneously, c) separating the solid phase with the bound cells from the remaining sample thereby providing blood plasma.

21 Claims, 6 Drawing Sheets

METHOD FOR OBTAINING BLOOD PLASMA FROM A WHOLE BLOOD SAMPLE

FIELD OF THE INVENTION

The present invention relates to an alternative method for obtaining blood plasma from a whole blood sample. The described technology may also be used for fractionating whole blood e.g. into three separate fractions: blood plasma, lysate of red blood cells and white blood cells. The resulting products are suitable for use in diagnostics such as e.g. virus or immunological diagnostics.

BACKGROUND OF THE INVENTION

Several methods are known in the prior art for obtaining blood plasma and/or fractions of whole blood. A classical, well-known approach for obtaining blood plasma or other blood fractions is based on the centrifugation of whole blood samples. The whole blood sample is centrifuged at high speed and, subsequently, the obtained fractions of interest are transferred into new vessels. However, this process requires special laboratory equipment such as centrifuges and furthermore, is difficult to automate.

Other methods for separating red and/or white blood cells from whole blood samples are also known in the prior art. E.g. U.S. Pat. No. 6,403,384 discloses a gel filtration method in which a cell-free blood plasma fraction is separated from the blood cells by means of capillary flow through the interstitial spacings between densely packed microspheres. U.S. Pat. No. 5,118,428 describes the partial agglutination of erythrocytes induced by the addition of certain acids, subsequently filtering off these erythrocytes by the flow through an appropriate material or removing the erythrocytes by centrifugation or decantation. U.S. Pat. No. 5,876,605 describes the production of blood plasma by means of filtration following the addition of an inorganic salt or amino acid to whole blood. U.S. Pat. No. 5,482,829 discloses the addition of osmotically active agents, i.e. which create a hypertonic solution without entering the cells themselves, and high molecular bridging substances for connecting the red blood cells and thereby enhancing the rate of sedimentation. U.S. Pat. No. 5,609,771 describes the separation of red blood cells from white blood cells by sequentially changing the position of a vessel filled with blood without adding chemicals, in order to permit efficient analysis of the white blood cells. U.S. Pat. No. 5,282,982 shows a blood washing method, in which the addition of substances promoting aggregation causes an accelerated sedimentation rate of the red blood cells and thus a shortened washing period. U.S. Pat. No. 7,754,499 discloses the specific isolation of blood constituents by means of magnetic particles, to which affinity markers such as for example antibodies are coupled, which specifically bind to the blood constituents representing target antigens. Finally, U.S. Pat. No. 3,552,928 describes a whole blood separating means, in which red blood cells are separated from whole blood by flow of the blood through a matrix containing certain amino acids and the resulting colourless fluid is contacted with a test reagent.

As is apparent by the above described prior art methods, the preparation of blood fractions such as blood plasma or white blood cells usually occurs manually and thus cannot be integrated into standard downstream processes that are often, respectively preferably performed on automated systems such as e.g. the isolation of nucleic acids from the obtained blood fractions. Furthermore, some of the respective methods are time consuming, expensive and/or need special equipment such as high speed centrifuges. A particular challenge is to provide a rapid, simple and cost-efficient method for obtaining blood plasma from whole blood that is of a suitable quality to be used in standard downstream applications such as diagnostic assays. Here, it is a particular challenge to provide a method for obtaining blood plasma that has a low risk of destroying red blood cells during the preparation. If the red blood cells are destroyed and accordingly, contaminate the obtained blood plasma, this can cause analytical errors in the downstream processes.

It is the objective of the present invention to provide an alternative method for obtaining blood plasma and/or one or more blood fractions from a whole blood sample. In particular, it was the objective to provide a respective method that is quick, suitable for automation and preferably overcomes one or more drawbacks of the prior art methods.

SUMMARY OF THE INVENTION

The present invention provides a rapid method for obtaining blood plasma that is based on the use of a magnetic solid phase and specific conditions that allow to efficiently bind red and white blood cells to the magnetic solid phase. The magnetic solid phase with the bound blood cell components can be removed from the remaining sample, thereby providing purified blood plasma of good quality. The technology inter alia has the advantage that it is rapid, efficient and suitable for automation and thus can be integrated into existing automatic systems that use blood plasma or a blood fraction such as white blood cells for nucleic acid isolation and/or analytical applications such as diagnostic applications.

According to a first aspect, a method for obtaining blood plasma from a whole blood sample is provided wherein said method comprises the following steps a) contacting the whole blood sample with a composition (A) comprising at least one carboxylic acid, wherein the addition of composition (A) and optionally further additives to the whole blood sample provides a sample mixture having a pH value that lies in a range from 2.5 to 5;

b) binding red and white blood cells to a magnetic solid phase;

wherein step a) and step b) can be performed sequentially or simultaneously, c) separating the magnetic solid phase with the bound cells from the remaining sample, thereby providing blood plasma.

As is shown in the examples, said method is suitable for rapidly providing blood plasma that is suitable for use in standard analytical applications, including diagnostic applications.

According to a second aspect, a method for fractionating whole blood is provided, said method comprising
 performing steps a), b) and c) according to the method according to the first aspect of the present invention, and additionally performing the following steps d) contacting the magnetic solid phase with the bound cells with a composition (B) that lyses red blood cells but not white blood cells;

e) separating the magnetic solid phase with the bound white blood cells from the lysate of red blood cells, and f) optionally washing the white blood cells and g) optionally eluting the white blood cells from the solid phase.

As is shown in the examples, said method is suitable for rapidly fractionating blood, thereby being able to provide a blood plasma fraction, a red blood cell fraction and a white blood cell fraction separately.

According to a third aspect, a method for obtaining nucleic acids from blood plasma and/or a blood fraction is provided, said method comprising
a) obtaining blood plasma and/or one or more blood fractions according to the method of the first or the second aspect and isolating nucleic acids from the obtained blood plasma and/or the one or more obtained blood fractions
or
b) (i) obtaining a blood fraction comprising white blood cells according to the method of the second aspect, (ii) lysing the white blood cells to release nucleic acids and (iii) optionally clearing the lysate, thereby providing a cleared lysate comprising the released nucleic acids.

According to a fourth aspect, the present invention pertains to the use of blood plasma and/or one or more blood fractions obtained according to the method of the first or the second aspect and/or nucleic acids obtained according to the third aspect, in an analytical assay, preferably a diagnostic assay.

According to a fifth aspect, a kit suitable for performing the method according to the first, second or third aspect is provided, said kit comprising
a) a magnetic solid phase, preferably carrying acidic groups, amino groups or both on its surface;
b) an acidic red blood cell aggregation composition (A) comprising at least one carboxylic acid and optionally comprising an osmotically active agent; and
c) optionally a red blood cell lysis composition (B).

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Figure 1:
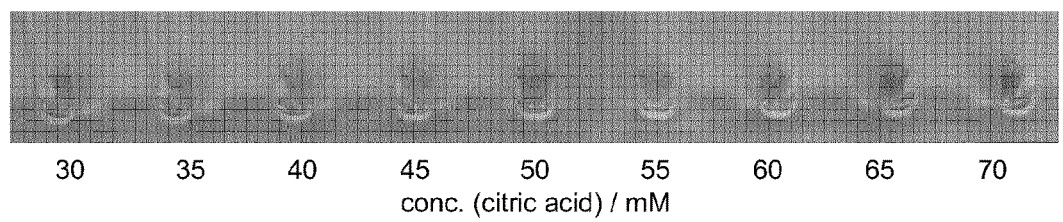
FIG. 1: Shows the blood plasma prepared according to example 2 using citric acid in composition (A). The figure shows the appearance of blood plasma depending on the used concentration (conc.) of citric acid in composition (A).

According to a first aspect of the present invention, a method for obtaining blood plasma from a whole blood sample is provided wherein said method comprises the following steps
a) contacting the whole blood sample with a composition (A) comprising at least one carboxylic acid, wherein the addition of composition (A) and optionally further additives to the whole blood sample provides a sample mixture having a pH value that lies in a range from 2.5 to 5;
b) binding red and white blood cells to a magnetic solid phase;
   wherein step a) and step b) can be performed sequentially or simultaneously,
c) separating the magnetic solid phase with the bound cells from the remaining sample thereby providing blood plasma.

Subsequently, we will explain the individual steps a) to c) and preferred embodiments thereof in detail.

In step a), the whole blood sample is contacted with a composition (A) which comprises at least one carboxylic acid. The addition of composition (A) and optionally further additives to the whole blood sample provides a sample mixture having a pH value that lies in a range from 2.5 to 5. Thus, the pH value of the sample mixture can be 2.5, 5 or any pH value between 2.5 and 5. Preferred sub-ranges are described below. As is shown by the examples, to induce the aggregation of red blood cells and prepare said cells for binding step b), it is important to add at least one carboxylic acid to the whole blood sample. Furthermore, the examples show that it is important to provide a specific pH value in the sample mixture, comprising the whole blood sample, composition (A) and optionally further additives (such as e.g. acids). As is shown in the examples, the pH value of the sample mixture must lie within a rather narrow pH range of 2.5 to 5. If the pH value of the sample mixture is above 5, the aggregation of the red blood cells is not effectively induced, what has the effect that the red blood cells cannot be efficiently bound to the magnetic solid phase and accordingly, cannot be efficiently removed. However, if the pH value of the sample mixture is below 2.5, red blood cell lysis begins, what is also not suitable for providing blood plasma of an acceptable quality that can be used in standard downstream applications, such as e.g. diagnostic assays. Thus, in step a), an acidic milieu is provided in the sample mixture which in combination with the carboxylic acid induces the aggregation of red blood cells without promoting red blood cell lysis and furthermore, establishes binding conditions that allow to bind the red and white blood cells to the magnetic solid phase.

According to one embodiment, composition (A) has due to the comprised carboxylic acid a pH value that provides upon mixture with the whole blood sample a pH value in the sample mixture that lies in the desired range of 2.5 to 5. However, as is shown by the examples, it is also possible to use a carboxylic acid in composition (A) which alone would not be suitable to establish the necessary pH value in the sample mixture. In this case, further additives may be added to composition (A), to the whole blood sample and/or to the sample mixture in order to adjust the pH value of the sample mixture to a pH value that lies in the range of 2.5 to 5. For this pH adjustment, any type of acid can be used including but not limited to inorganic as well as organic acids. Furthermore, it is also within the scope of the present invention to use a combination of two or more acids to establish the desired pH value. Also other acidifying reagents can be used, respectively can be added to establish the desired pH value in the sample mixture. Preferably, the acid that is used for said pH adjustment is a non-oxidizing acid. Suitable inorganic acids that can be comprised in composition (A) and/or can added separately to establish the desired pH value in the sample mixture are preferably selected from the group consisting of hydrogen halides, preferably hydrochloric, hydrobromic and hydroiodic acid, sulphuric acid and phosphoric acid, wherein hydrochloric acid is especially preferred. Suitable organic acids are preferably selected from the group consisting of sulphuric acids and carboxylic acids. Any acids described herein may also be used in form of a salt and such an embodiment is according to one embodiment encompassed by the term "acid".

To induce the aggregation, in particular the agglutination of the red blood cells in the sample mixture and to establish the binding conditions for step b), the whole blood sample is contacted with composition (A) and optionally one or more further additives. Composition (A) comprises at least one carboxylic acid. The term "carboxylic acid" as used herein also refers to salts of carboxylic acids. Composition (A) may also comprise more than one carboxylic acid. However, it is preferred that composition (A) only comprises one type of carboxylic acid. The addition of at least one carboxylic acid to the whole blood sample is as shown by the examples important in order to avoid the lysis of red blood cells during step a) and/or b). As is shown by the examples, merely establishing a pH value which lies in a range of 2.5 to 5 in the sample mixture is not sufficient in order to be able to provide blood plasma of an adequate quality. In the absence of a carboxylic acid, the red blood cells are rapidly lysed at said acidic pH values.

Thus, in step a) the whole blood sample is contacted with composition (A) which comprises at least one carboxylic acid and optionally is contacted with further additives to establish a sample mixture having a pH value which lies in the range of 2.5 to 5 and comprising the carboxylic acid of composition (A) in an amount sufficient to induce aggregation, in particular agglutination of the red blood cells, wherein however, no substantial lysis of the red blood cells occurs. Suitable embodiments for achieving respective contacting/incubation conditions are described in detail below.

Preferably, the pH value of the sample mixture is adjusted either by composition (A) alone or by performing additional pH adjustments, e.g. by adding additional acidifying compounds such as acids. Suitable acids are described above. Preferably, the pH value of the resulting sample mixture lies in a range that is preferably selected from 2.5 to 4.75, 2.55 to 4.65, 2.6 to 4.6, 2.65 to 4.55, 2.7 to 4.5, 2.75 to 4.45, 2.75 to 4.4, 2.8 to 4.35, 2.85 to 4.3, 2.9 to 4.25, 2.95 to 4.2, 3.0 to 4.15, 3.0 to 4.1, 3.0 to 4.05, 3.0 to 4.0, 3.0 to 3.95, 3.0 to 3.9, 3.0 to 3.85, 3.0 to 3.8 and 3.0 to 3.75. As is shown in the examples, in particular the narrower pH ranges, in particular from 3 to 4 and 3 to 3.75 provide excellent results in that a blood plasma can be obtained, which is clear and uncoloured. Therefore, it is preferred to provide a pH value in the sample mixture comprising the whole blood sample, composition (A) and optionally one or more further additives that lies in said narrower pH ranges.

As described above, in order to achieve a pH value in the sample mixture that lies in the range of 2.5 to 5 and preferably in the narrower ranges described above, additional acids such as hydrochloric acid can be included in composition (A) or can be added separately to the sample mixture if the carboxylic acid(s) comprised in composition (A) is not sufficient in order to adjust the pH value of the sample mixture when the whole blood sample is mixed with composition (A).

According to one embodiment, composition (A) comprises the at least one carboxylic acid in a concentration that lies in a range selected from 25 mM to 1.25M, 25 mM to 1M, 25 mM to 750 mM, 25 mM to 500 mM, 30 mM to 300 mM, 30 mM to 250 mM, 30 mM to 200 mM, 30 mM to 150 mM, 30 mM to 100 mM, 50 mM to 100 mM and 30 mM to 75 mM. The preferred concentration or concentration range depends on the chosen carboxylic acid and on the ratio that is used when mixing composition (A) with the whole blood sample. Suitable concentrations can be determined by the skilled person following the teachings of the present application. It is important to choose a concentration of carboxylic acid in the sample mixture which in conjunction with the suitable and preferred pH ranges specified herein and in conjunction with further additives that may be added optionally such as e.g. salts does not destroy, in particular does not induce bursting of the red blood cells comprised in the sample mixture. The osmotic activity of all compounds comprised in the sample mixture shall be chosen such to lie within a range which does not destroy, in particular does not induce or promote bursting of the erythrocytes comprised in the sample mixture. Suitable concentrations for the at least one carboxylic acid and the optional further additives comprised in the sample mixture can be determined by the skilled person when following the teachings of the present invention. According to one embodiment, the concentration of the at least one carboxylic acid in the sample mixture comprising the whole blood sample, composition (A) and optionally further additives lies in a range selected from 10 mM to 850 mM, 12.5 mM to 750 mM, 15 mM to 650 mM, 17.5 mM to 550 mM, 20 mM to 400 mM, 20 mM to 350 mM, 20 mM to 300 mM, 22.5 mM to 250 mM, 25 mM to 200 mM, 27.5 mM to 175 mM, 30 mM to 150 mM, 30 mM to 125 mM, 30 mM to 100 mM, 30 mM to 80 mM, 30 mM to 75 mM and 30 mM to 50 mM.

Composition (A) can be mixed with the blood sample e.g. in a ratio selected from 100 (composition (A)):1 (blood) to 1 (composition (A)):1 (blood). Preferred ratios are selected from 50:1 to 2:1, 25:1 to 3:1, more preferred 10:1 to 3:1, most preferred 7:1 to 3:1.

According to one embodiment, the at least one carboxylic acid comprised in composition (A) is selected from the following group:
 a) mono-, di- or tricarboxylic acids,
 b) citric acid, ascorbic acid and malic acid,
 c) citric acid,
 d) a carboxylic acid carrying at least one additional functional group;
 e) amino acids and derivatives thereof,
 f) glycine, threonine and alanine, and
 g) glycine.

Monocarboxylic acids include but are not limited to formic, acetic, lactic and ascorbic acid. Dicarboxylic acids include but are not limited to oxalic, malonic, maleic, fumaric, malic, tartaric and gluconic acid. Tricarboxylic acids include but are not limited to citric acid. These mono-, di- or tricarboxylic acids may optionally comprise one or more hydroxy groups. Tricarboxylic acids are particularly preferred. According to one embodiment, the carboxylic acid comprised in composition (A) is selected from citric acid, ascorbic acid, maleic acid, malic acid and malonic acid. Citric acid, ascorbic acid and malic acid are preferred.

As is shown by the examples citric acid provided particularly good results. Said results were also superior to that achieved with ascorbic acid, maleic acid, malic acid and malonic acid. Thus, the use of citric acid is preferred. Suitable concentrations and concentration ranges were described above in conjunction with the carboxylic acid in general and also apply with respect to citric acid as embodiment of a carboxylic acid. According to one embodiment, composition (A) comprises citric acid preferably in a concentration selected from a range of 25 mM to 150 mM, 25 mM to 125 mM, 25 mM to 100 mM, 25 mM to 85 mM, 25 mM to 75 mM, 30 mM to 70 mM and 35 mM to 65 mM. Most preferred, composition (A) comprises citric acid in a concentration of approx. 50 mM. The concentration of citric acid in the sample mixture may be selected from one of the following ranges 10 mM to 125 mM, 12.5 mM to 100 mM, 15 mM to 75 mM, 17.5 mM to 60 mM, 20 mM to 55 mM, 22.5 mM to 50 mM, 25 mM to 45 mM and 27.5 mM to 40 mM.

According to one embodiment, the carboxylic acid comprised in composition (A) comprises at least one additional functional group and preferably is an amino acid, preferably a proteinogenic amino acid, or a derivative thereof. According to one embodiment, the amino acid is selected from the group consisting of glycine, alanine, arginine, glycylglycine, histidine and threonine or derivatives thereof, more preferred selected from glycine, threonine and alanine. If using an amino acid, then it is preferred that composition (A) comprises glycine. Preferably, composition (A) comprises the amino acid, preferably glycine, or a salt thereof in a concentration of at least 20 mM, preferably selected from the ranges of 25 mM to 1.25M, 25 mM to 1M, 25 mM to 750 mM, 25 mM to 500 mM, 30 mM to 300 mM, 30 mM to 250 mM, 30 mM to 200 mM, 35 mM to 175 mM, 40 mM to 150 mM, 45 mM to 135 mM, 50 mM to 125 mM and 50 mM to 100 mM. According to one embodiment, the concentration of glycine in the sample mixture comprising the whole blood sample, composition (A) and optionally further additives lies in a range selected from 15 mM to 850 mM, 17.5 mM to 750 mM, 20 mM to 650 mM, 22.5 mM to 550 mM, 25 mM to 350 mM, 25 mM to 300 mM, 25 mM to 250 mM, 25 mM to 200 mM, 27.5 mM to 175 mM, 30 mM to 150 mM, 30 mM to 125 mM, 30 mM to 100 mM, 30 mM to 90 mM, 30 mM to 85 mM, 30 mM to 80 mM.

If using glycine as carboxylic acid in composition (A), e.g. in a concentration of 50 mM or above, the pH value of the composition (A) is above pH 5.5. Accordingly, glycine as carboxylic acid would—alone—not be suitable to adjust the pH value in the sample mixture to the desired pH range of 2.5 to 5. Thus, to achieve the necessary pH value in the sample mixture it is preferred that the pH value of composition (A) is adjusted preferably by adding an acid such as hydrochloric acid (HCl) to obtain a pH value in composition (A) that, if composition (A) is mixed with the whole blood sample, adjusts the pH value in the resulting sample mixture to a pH value that lies in the range of 2.5 to 5 and preferably in the preferred narrower pH ranges described above. Preferably, the pH value of composition (A) is 3.5 or less, 3.25 or less, 3 or less, 2.75 or less, 2.5 or less, 2 or less, 1.75 or less or 1.5 or less. The concentration of HCl in composition (A) comprising 50 mM glycine is preferably at least 20 mM, at least 25 mM and preferably at least 30 mM. However, as described above, it is also within the scope of the present invention to adjust the pH value of the sample mixture by adding one or more further additives such as acidifying reagents, preferably acids such as hydrochloric acid, separately from composition (A) to the whole blood sample. This can be done prior to, after or at the same time when composition (A) is added to the whole blood sample.

According to one embodiment, at least one osmotically active agent is added in step a) to the whole blood sample. Said osmotically active agent has the purpose to prevent or at least delay cell lysis. As is shown in the examples, adding an osmotically active agent has the advantage that red blood cell lysis can be delayed. This allows using longer incubation times in step a) and/or b) before red blood cell lysis begins. This is an important advantage that simplifies the handling and makes the method according to the present invention less error-prone. Furthermore, the extended incubation periods that are possible if an osmotically active agent is added in step a) facilitates the automation of the method according to the present invention, for example if using robotic systems.

According to one embodiment, the osmotically active agent that is used for stabilization has one or more of the following characteristics:
 i) it is uncharged;
 ii) it stabilizes cells comprised in the sample by inducing cell shrinking;
 iii) it is cell impermeable;
 iv) it is water-soluble;
 v) it is a hydroxylated organic compound; preferably comprising at least 3 hydroxy groups.
 vi) it is a polyol;
 vii) it is a hydroxy-carbonyl compound;

viii) it is a carbohydrate or a sugar alcohol; and/or
ix) it is a carbohydrate selected from the group consisting of trehalose, sucrose and glycerine.

As described above, the osmotically active agent acts as a stabiliser which prevents cell lysis, in particular red blood cell lysis, in the sample mixture. Preferably, the osmotically active agent is comprised in composition (A). However, it may also be added separately to the whole blood sample or to the sample mixture that is obtained when contacting composition (A) with the whole blood sample. If comprised in composition (A) it is preferably comprised therein in a concentration selected from 5% (w/v) to 50% (w/v), 7.5% (w/v) to 45% (w/v), 10% (w/v) to 40% (w/v), 10% (w/v) to 35% (w/v), 15% (w/v) to (30% (w/v), 15% (w/v) to 25% (w/v). The concentration of osmotically active agent in the sample mixture may be selected from one of the following ranges 2.5% (w/v) to 45% (w/v), 5% (w/v) to 40% (w/v), 7.5% (w/v) to 35% (w/v), 10% (w/v) to 30% (w/v), 12.5% (w/v) to 25% (w/v), 15% (w/v) to 20% (w/v), Preferably, the osmotically active agent is a hydroxylated organic compound, preferably comprising at least 3 hydroxyl groups. More preferably, the osmotically active agent is a carbohydrate or a carbohydrate derivative such as a hydrogenated form of a carbohydrate. Suitable carbohydrates and derivatives thereof from which the osmotically active agent can be selected include but are not limited to monosaccharides, disaccharides, oligosaccharides, polysaccharides, non-reducing sugars and sugar alcohols. Preferably, the osmotically active agent is selected from the group consisting of trehalose, sucrose and glycerine. As is shown by the examples, these osmotically active agents are particularly suitable to prevent red blood cell lysis in the sample mixture. Suitable and preferred concentration ranges are described above and below. Also combination of osmotically active agents can be used.

According to one embodiment, the osmotically active agent is trehalose. If comprised in composition (A), trehalose is preferably comprised in a concentration of at least 15% (w/v), preferably in the range of 20 to 25% (w/v). According to another embodiment, the osmotically active agent is sucrose. If comprised in composition (A), sucrose is preferably comprised in a concentration of at least 5% (w/v), preferably at least 7.5% (w/v), more preferred at least 10% (w/v). Preferably sucrose is comprised in composition (A) in a concentration selected from the range of 10 to 25% (w/v). According to another embodiment, the osmotically active agent is glycerine. If comprised in composition (A), glycerine is preferably comprised in a concentration of least 5% (w/v), preferably at least 7.5% (w/v), more preferred at least 10% (w/v). Preferably sucrose is comprised in composition (A) in a concentration selected from the range of 10 to 25% (w/v), preferably in the range of 10 to 20% (w/v).

In some embodiments, composition (A) additionally comprises an inorganic salt, preferably an alkali metal salt. More preferably, the inorganic salt is sodium chloride or potassium chloride. In composition (A), the alkali metal salt preferably has a concentration selected from at least 30 mM, at least 40 mM, at least 50 mM, at least 60 mM, at least 75 mM and at least 100 mM. Adding a salt may have depending on the concentration of the carboxylic acid in composition (A) and depending on the concentration of the carboxylic acid in the sample mixture the advantage that the salt may support maintaining an isotonic milieu which is beneficial to prevent or at least reduce cell lysis, in particular red blood cell lysis. The suitable and preferred concentration of such salt also depends on the concentration of the carboxylic acid that is used. As described above, the osmotic activity of all compounds added to the blood sample is chosen such that cell lysis is not induced. Composition (A), when added to the blood sample, does not have cell lysing properties.

Furthermore, composition (A) may comprise an additional buffering compound, in particular if the comprised carboxylic acid is not sufficient to achieve the desired buffering effect.

In step b), red and white blood cells are bound to a magnetic solid phase. Using a magnetic solid phase, such as for example magnetic particles, has the advantage that the method according to the present invention can be performed very rapidly and additionally, is suitable for automation. For example, it can be performed on a robotic system suitable for processing a magnetic solid phase, such as magnetic particles. Such robotic systems are very common for isolating nucleic acids and thus, the method according to the present invention can be easily integrated into a respective workflow. The magnetic solid phase that is used according to the present invention has a surface which allows binding of the aggregated red blood cells and white blood cells from the sample mixture. Details of the sample mixture, in particular suitable and preferred pH values, suitable and preferred concentrations and embodiments of the carboxylic acid and optionally, suitable and preferred concentrations and embodiments of the osmotically active agent and further optional additives were described in detail above in conjunction with step a). Preferably, the red and white blood cells bind, e.g. bind or adsorb unspecifically to the magnetic solid phase. Therefore, it is not necessary to functionalize the magnetic solid phase with specific affinity surface groups or affinity surface agents such as antibodies that would allow to specifically bind the red and white blood cells, e.g. by binding specific target structures on the cell surface. The aggregated red blood cells and the white blood cells comprised in the sample mixture bind under the conditions established in the sample mixture to the magnetic solid phase.

The magnetic solid phase may be superparamagnetic, ferromagnetic, ferrimagnetic or paramagnetic. The magnetic solid phase responds to a magnetic field. The magnetic solid phase is capable of binding red and white blood cells comprised in the sample mixture that is obtained when contacting composition (A) and optionally further additives with the whole blood sample. Preferably, the magnetic solid phase carries surface groups that promote unspecific binding of the aggregated red blood cells and the white blood cells to the solid phase. According to one embodiment, binding to the magnetic solid phase occurs, respectively is promoted, by ionic interactions.

Preferably, the surface groups are ionisable groups such as cationic or anionic exchange groups. Also suitable are functional groups such as trimethylsilyl groups. Furthermore, also combinations of respective surface groups such as a combination of cationic exchange groups and anionic exchange groups can be used. The magnetic solid phase can be functionalized with polycations or polyanions to provide respective surface groups. According to a preferred embodiment, the magnetic solid phase comprises acidic surface groups, preferably selected from carboxyl groups, phosphoric acid groups and sulphuric acid groups. It is particularly preferred that the magnetic solid phase comprises carboxyl groups at its surface. A respective surface can be provided e.g. by functionalization with appropriate ligands. As is shown by the examples, using a magnetic solid phase comprising carboxyl groups on its surface, such as carboxylated magnetic particles, allows to efficiently produce blood plasma according to the teachings of the present invention.

A carboxylated solid phase exhibits a very good binding capacity for red and white blood cells under the binding conditions that are established in the sample mixture according to the teachings of the present invention. Details were described above, it is referred to the above disclosure.

Also suitable are cationic surface groups, in particular surface groups comprising one or more amino groups. Preferably, the magnetic solid phase is functionalised with a surface ligand comprising at least one amine group, e.g. comprising at least one primary, secondary, tertiary or quarternary amino group. Mono, diamines as well as polyamines and polyimines can be used for functionalization. Thus, the magnetic solid phase can be functionalised, e.g. coated with suitable amines or imines such as polymers of ethylenimine. As is shown by the examples, a magnetic solid phase carrying amino groups on their surface is also suitable to provide blood plasma according to teachings of the present invention. Furthermore, as is shown by the examples, various magnetic beads comprising carboxyl groups on their surface can be used. Carboxyl groups are thus preferred and can be used either alone or in combination with other functional groups such as e.g. amine groups. Furthermore, the examples show that various other surface modifications are suitable to allow binding of red and white blood cells under the conditions established in the sample mixture as described herein, in particular ionisable groups including but not limited to functionalizations with compounds comprising amine groups, polyethylenimine, polyacrylic acid, succinic acid, trimethylsilyl (TMS) groups and combinations thereof.

According to one embodiment, a magnetic solid phase is used which comprises acidic groups, preferably carboxyl groups, as well as cationic groups such as amino groups, preferably primary, secondary or tertiary amino groups on their surface. As is shown in the examples, a magnetic solid phase carrying both types of surface groups provides very good results and thus is particularly suitable to provide blood plasma according to the present invention. A respective surface can be provided e.g. by functionalization with appropriate ligands.

The respective surface groups described above may form part of the solid phase or they can be bound covalently or non-covalently to the surface of the magnetic solid phase, e.g. using appropriate ligands that introduce said groups or by using a coating method. Preferably, they are covalently bound to the surface of the solid phase.

In any case, the surface of the magnetic solid phase allows binding of red and white blood cells from the sample mixture and hence under the binding conditions described above.

Preferably, magnetic particles are used. Preferably, the magnetic particles comprise a coated magnetic core; the magnetic particles may also comprise more than one magnetic core. The coating can be provided by polymers, metal oxides, polysaccharides and/or silica. Preferably, the magnetic particles carry on their surface one or more of the above described surface groups, preferably carboxyl groups, amino groups or a mixture of both.

In step b), the red blood cells and the white blood cells are bound to the magnetic solid phase. As is shown in the examples, step a) and step b) can be performed sequentially or simultaneously. If step a) and step b) are performed sequentially, the sample mixture that was obtained in step a) is contacted with the magnetic solid phase for a sufficiently long period of time, i.e. a period of time which allows the aggregated red blood cells as well as the white blood cells to bind to the magnetic solid phase. In this sequential embodiment, the whole blood sample is contacted with composition (A) and optionally further additives for a sufficiently long period of time to induce the aggregation of red blood cells in the sample mixture, wherein however, no substantial lysis of the red blood cells occurs. As described in detail above for step a), the sample mixture has a pH value that lies in a range from 2.5 to 5 and comprises at least one carboxylic acid that was introduced by composition (A). After the aggregation of the red blood cells was accordingly induced, the magnetic solid phase is contacted with the sample mixture, for example in pure form or in form of a suspension. Preferably, the magnetic solid phase, preferably magnetic particles, is used in form of a suspension. The resulting mixture is incubated to bind the aggregated red blood cells and the white blood cells to the magnetic solid phase. The overall incubation time of step a) combined with step b) should be chosen such that no substantial lysis of the red blood cells occurs. Suitable incubation times are described herein.

In a preferred embodiment, steps a) and b) are performed simultaneously. Thereby, the preparation time can be shortened and furthermore, it was found that in this embodiment binding of the cells to the magnetic solid phase is even more efficient as is also shown by the examples. Therefore, the whole blood sample can be contacted with composition (A) in the presence of the magnetic solid phase. Here, several embodiments are feasible. The magnetic solid phase, composition (A) and the whole blood sample can be contacted in any order. Furthermore, the magnetic solid phase can be suspended in composition (A) and the respective suspension of composition (A) and the magnetic solid phase is then contacted with the whole blood sample. This embodiment is particularly preferred if magnetic particles are used as magnetic solid phase. The resulting sample mixture comprising composition (A), optionally further additives, the whole blood sample and the magnetic solid phase is then incubated for a sufficient period of time to allow the aggregation of the red blood cells and binding of the red and white blood cells comprised in the sample mixture to the magnetic solid phase.

The sample mixture which optionally also comprises the magnetic solid phase if step a) and step b) are performed simultaneously, is incubated for a time sufficient to aggregate the red blood cells and to bind the red blood cells and the white blood cells to the solid phase. Incubation during step a) and step b) occurs such that no substantial lysis of the red blood cells occurs as otherwise the quality of the obtained blood plasma would be decreased. The suitable or feasible incubation time depends on the composition of the sample mixture and accordingly, depends on composition (A) and the optional further additives that are added separately and accordingly, the further additives that may be included in the sample mixture. As was shown by examples, an incubation time as short as 15 seconds is already sufficient in order to efficiently aggregate the red blood cells and allow binding of the red blood cells and the white blood cells to the magnetic solid phase, in particular if carboxylated magnetic particles are used as magnetic solid phase. Furthermore, if an osmotically active agent such as trehalose, sucrose or glycerine is used as further additive for stabilization, the incubation time can be considerably prolonged because red blood cell lysis is delayed. Suitable overall incubation periods for step a) and b) (step a)+step b)) are selected from 10 min or less, 8 min or less, 7 min or less, 6 min or less, 5 min or less, 4 min or less or 3 min or less. Suitable incubation times can be selected from the following ranges: 15 sec to 10 min, 15 sec to 7 min, 15 sec to 6.5 min, 15 sec to 6 min, 30 sec to 5.5 min, 45 sec to 5 min, 15 sec to 4.5 min, 15 sec to 4 min, 15 sec to 3.5 min and 30 sec to 3 min. It is preferred that the respective incubation times are not exceeded when performing step a) and step b) either simultaneously or sequentially and hence are not exceeded prior to performing step c). As is shown by the examples, longer incubation times are also not necessary, what is advantageous as the overall time that is needed to prepare the blood plasma is considerably reduced. Furthermore, the suitable or maximum incubation period that should not be exceeded as otherwise red blood cell lysis could begin does not only depend on the composition of the sample mixture but also depends on the type of whole blood sample that is processed. E.g. it was found that the storage time of the whole blood sample to be processed has an influence on the suitable incubation time. If the whole blood sample has been stored for a longer time, such as for example several days or even a week, the suitable incubation times are shorter than the incubation times that are suitable if fresh blood samples are processed. I.e. red blood cell lysis occurs earlier in whole blood samples that were stored for several days or even a week. If the obtained blood plasma has a dark colour this indicates that red blood cell lysis occurred.

In step c), the magnetic solid phase to which the red and white blood cells were bound in step b) is separated from the remaining sample, thereby providing purified blood plasma. As is shown by the examples, the method according to the present invention is highly efficient and the magnetically produced blood plasma is substantially free of cellular components as they can be efficiently removed by using the method according to the present invention. Separation preferably occurs by the aid of a magnet. Here, several embodiments are feasible to magnetically separate the magnetic solid phase, which preferably is provided by magnetic particles.

According to one embodiment, a magnet is placed at the bottom or side of the reaction vessel comprising the sample mixture, thereby collecting the magnetic solid phase, preferably the magnetic particles, including the bound red and white blood cells at the bottom or side of the reaction vessel. The remaining sample which corresponds to the purified blood plasma can then for example be decanted or removed e.g. by the aid of a pipette. This can be performed manually or by using an automated system, preferably a pipetting robot that allows to process magnetic particles. Suitable systems are known and available in the prior art and thus, do not need any further description here.

In an alternative system that is also well-known and established for processing magnetic particles, a magnet plunges into the reaction vessel to collect and remove the magnetic particles together with the bound red and white blood cells from the reaction vessel. After removal of the magnetic particles which carry the bound red and white blood cells, the purified blood plasma is left behind in the reaction vessel. Respective robotic systems are also well known in the prior art, and accordingly do not need a detailed description here.

The blood plasma that is obtained by the method according to the present invention is usually if at all only slightly coloured and preferably is substantially colourless and clear. The red colour of blood is caused by the haemoglobin of the red blood cells. When producing the blood plasma according to the teachings of the present invention, the red colour has substantially disappeared in the obtained blood plasma because the red blood cells were effectively bound to the magnetic solid phase using the binding conditions in the sample mixture as described above and were removed together with the magnetic solid phase. Furthermore, if the blood plasma is colourless or only slightly coloured (preferably yellow or orange), this shows that no or at least no significant lysis of red blood cells occurred during the preparation and accordingly shows that the obtained blood plasma is not substantially contaminated with a red blood cell lysate. However, it is important to note that the colour of the obtained blood plasma may also naturally vary from blood donor to blood donor, respectively patient to patient and may also depend on its health status. Therefore, the magnetically obtained blood plasma may be yellow or otherwise slightly coloured due to the status of the blood donor. Moreover, the blood plasma obtained when following the teachings of the present invention is not turbid but preferably is clear what indicates that not only the red blood cells but also white blood cells were efficiently removed. As is shown by the examples, the method according to the present invention can be performed equally efficient as conventional, more time consuming plasma preparation methods that are based e.g. on centrifugation steps. Furthermore, as is shown by the examples, the present invention provides blood plasma that is suitable for use in standard applications, such as for example standard diagnostic assays or nucleic acid isolation methods. In respective standard applications, the magnetically obtained blood plasma is equally suitable as blood plasma that was obtained using conventional methods. However, the method according to the present invention is more rapid, does not need centrifugation equipment and is suitable for automation. Therefore, a highly simple, automatable and efficient method for obtaining blood plasma is provided by the present invention.

According to a second, closely related aspect, a method for fractionating whole blood is provided, said method comprising performing steps a), b) and c) according to claim 1, and additionally performing the following steps d) contacting the solid phase with the bound cells with a composition (B) that lyses red blood cells but not white blood cells;

e) separating the solid phase with the bound white blood cells from the lysate of red blood cells and f) optionally washing the white blood cells and g) optionally eluting the white blood cells from the solid phase.

As is apparent, steps a) to c) are the same as in the method according to the first aspect according to the present invention. Thus, with respect to details of steps a) to c) it is referred to the above detailed disclosure. Step a) and step b) can be again performed sequentially or preferably, simultaneously. After step c), blood plasma is provided as first fraction and accordingly, can be used for further analysis, if desired. However, the blood plasma may also be discarded if the main interest is on one of the other blood fractions that can be obtained with the respective method.

After step c), the magnetic solid phase to which the aggregated red and white blood cells were bound, may optionally be washed one or more times with an appropriate washing solution to remove remainders of blood plasma. For this purpose, a PBS buffer (phosphate buffered saline) may be used. A respective washing step is optional and suitable washing conditions are also known in the prior art.

Because a magnetic solid phase is used, after binding of the red and white blood cells to the magnetic solid phase, wherein preferably magnetic particles are used, these cells can be collected or separated from the blood plasma which surrounds the cells by the aid of a magnetic field. As described above, this separation step may easily be performed automatically. In a preferred embodiment, a magnet is applied externally to the vessel in which the blood cells and the magnetic beads are located, preferably for 1 to 2 min, more preferably for 1 min, and the remainder of the sample, i.e. the blood plasma is removed from the vessel, for example decanted off, or removed with the aid of a suitable device, for example drawn off with the aid of a pipette. Furthermore, as described above, it is also possible to remove the magnetic particles from the vessel by using a magnet that plunges into the vessel and collects the magnetic particles with the bound cells. The collected cells can be transferred together with the magnetic particles into a new vessel. The magnetic particles together with the blood cells can optionally be resuspended in a suitable wash medium and thereby washed, wherein after said washing step a magnetic field is again applied to the vessel and the wash medium is removed from the vessel or the magnetic particles carrying the bound cells are removed transferred into a new reaction vessel. The present method therefore allows a particularly gentle and rapid handling of the blood cells.

In step d), the magnetic solid phase to which the red and white blood cells are still bound is contacted with a composition (B) that lyses red blood cells but not white blood cells. Accordingly, in step d), red blood cells are selectively lysed by using a red blood cell lysis composition (B) which lysis erythrocytes, i.e. red blood cells, but which does not substantially lyse white blood cells. Any red blood cell lysis buffer known in the prior art can be used for this purpose, respective red blood cell lysis buffers are also commercially available. Suitable examples of standard red blood cell lysis buffers include but are not limited to the erythrocyte lysis buffer ELB1 (320 mM sucrose, 50 mM Tris/Cl pH 7.5, 5 mM $MgCl_2$, 1% TRITON™ X-100) or ELB2 (155 mM $NH_4Cl$, 10 mM $KHCO_3$).

In step d), the white blood cells are not lysed and accordingly, remain bound to the magnetic solid phase. In step e), the magnetic solid phase—with the white blood cells being bound thereto—is then separated from the lysate of red blood cells. As a magnetic solid phase is used, preferably magnetic particles as described above, this separation step can be performed again by the aid of a magnetic field. Suitable non-limiting embodiments for performing a magnetic separation are described above. After performing step e), a lysate of red blood cells is obtained as a second fraction, whereas the white blood cells being bound to the magnetic solid phase are obtained as third fraction. The lysate of red blood cells may be subjected to further analyses, preferably to diagnostic analyses or may be discarded.

In optional step f), the white blood cells that are still bound to a magnetic solid phase may again be washed one or more times to remove remainders of the red blood cell lysate that was obtained in step e). Suitable washing solutions include but are not limited to PBS. A respective washing step is optional.

Furthermore, if desired, the white blood cells can be processed further while they are still bound to the magnetic solid phase. Such further processing while the white blood cells are bound to the magnetic solid phase can be done directly after step d) or after optional step f). Non-limiting embodiments are described subsequently for the white blood cell fraction. In particular, nucleic acids can be released from the white blood cells using appropriate lysing conditions and if desired, can be purified thereafter.

In optional step g), the white blood cells may be separated from the magnetic solid phase and accordingly can be eluted therefrom e.g. by contacting the magnetic solid phase carrying the bound white blood cells with an elution composition under suitable conditions under which the white blood cells detach from the magnetic solid phase. Thereby, the white blood cells and the magnetic solid phase are separated from each other, i.e. the white blood cells are no longer bound to the magnetic solid phase. After elution, the magnetic solid phase and the white blood cells may be present in form of a suspension, e.g. if magnetic particles are used as magnetic solid phase. Said eluate comprising the magnetic solid phase and the white blood cells may be directly processed as white blood cell fraction, e.g. in order to obtain nucleic acids therefrom as will also be described in further detail subsequently.

In an optional step h), the magnetic solid phase can be separated from the eluate using a magnetic field, thereby providing a white blood cell fraction which does not comprise the magnetic solid phase that was used for binding the white blood cells. The respective white blood cell fraction can be subjected to further analysis, for example visual inspection of the obtained white blood cells, flow cytometry analysis, FACS analysis, immunostaining or any other analysis that is performed on a white blood cell fraction known in the prior art. Furthermore, nucleic acids may be obtained, preferably isolated from the white blood cells as will also be described subsequently.

According to one embodiment, the white blood cells are lysed. A respective lysis step may occur in the presence of the magnetic solid phase, after the white blood cells were separated from the magnetic solid phase or even may occur while the white blood cells are still bound to the magnetic solid phase. Any composition being suitable for the lysis of white blood cells can be used and several lysis compositions are known in the prior art and may be used for this purpose. For example commercially available white blood cell lysis buffers may be used, for example the lysis buffer provided in the QIAAMP® DNA Mini Kit (QIAGEN). Lysis compositions that are suitable for the lysis of white blood cells are also disclosed in WO 2010/003493 A1. Due to the lysis of white blood cells, nucleic acids are released and the lysate comprising the released nucleic acids can then be used either directly in an analytical method (e.g. an amplification reaction) or nucleic acids may be isolated from the lysate. Suitable embodiments are also described below in conjunction with the third aspect of the present invention.

The whole blood sample that is processed in the methods according to the present invention may be of human as well as of animal origin and preferably is of human origin. The whole blood sample that is processed using the methods of the present invention may be stabilised and preferably may comprise an anticoagulant for stabilisation. Anticoagulants that are regularly used to stabilize whole blood samples may be e.g. selected from the group consisting of heparin, ethylenediamine tetraacetic acid, citrate, oxalate, and any combination thereof. In an advantageous embodiment, the anticoagulant is a chelating agent. A chelating agent is a compound that is capable of forming coordinate bonds with metals through two or more atoms of the organic compound. Preferably, it is an organic compound. Suitable chelating agents include, but are not limited to diethylenetriaminepentaacetic acid (DTPA), ethylenedinitrilotetraacetic acid (EDTA), ethylene glycol tetraacetic acid (EGTA) and N,N-bis(carboxymethyl)glycine (NTA). According to a preferred embodiment, EDTA is used. As used herein, the term "EDTA" indicates inter alia the EDTA portion of an EDTA compound such as, for example, $K_2EDTA$, $K_3EDTA$ or $Na_2EDTA$. Respective compounds are suitable as anticoagulant to stabilize the whole blood sample. Usually, a respective stabilization occurs directly upon or during collection of the whole blood sample.

According to a third aspect of the present invention, a method for obtaining nucleic acids from blood plasma and/or at least one blood fraction such as for example a white blood cell fraction is provided. Characteristic for the respective method is that blood plasma and/or a blood fraction such as for example a white blood cell fraction is obtained from a whole blood sample using the methods according to the first or second aspect according to the present invention. Details of said first and second aspect were described above, it is referred to the above disclosure. Afterwards, nucleic acids are obtained from the blood plasma and/or one or more of the other blood fractions.

According to one embodiment of said third aspect, nucleic acids are isolated from obtained blood plasma and/or from one or more of the obtained blood fractions, such as in particular from the white blood cell fraction. As described above, the white blood cell fraction may or may not comprise the magnetic solid phase that was used for binding the blood cells. Suitable nucleic acid isolation methods are known in the prior art and include but are not limited to extraction, solid-phase extraction, silica-based purification methods, nucleic acid isolation procedures using chaotropic agents and/or at least one alcohol and a nucleic acid binding solid phase, magnetic particle-based purification, phenol-chloroform extraction, chromatography, anion-exchange chromatography (using anion-exchange surfaces), filtration, precipitation, and combinations thereof. Such methods are known in the prior art and thus, do not need a detailed description here. Preferred embodiments which enable a simple and rapid nucleic acid isolation that is also suitable for automation are described below. Preferably, the nucleic acids are isolated using an automated system. Automated systems allow to process large sample quantities.

Preferably, the nucleic acids are isolated from the obtained blood fraction, preferably the blood plasma or the white blood cells by the aid of a nucleic acid binding solid phase, preferably by using a magnetic nucleic acid binding solid phase such as for example magnetic particles. Using magnetic particles for the isolation of nucleic acids has the advantage, that the whole procedure starting from the whole blood sample down to the isolated nucleic acids can be performed on a robotic system that is capable of handling magnetic particles. Suitable systems are described above and are also known in the prior art. Preferably, the nucleic acid isolation involves a lysis step to digest the sample, for example the blood plasma and/or the white blood cells to release the nucleic acids and then subsequently isolating the nucleic acids from the digested/lysed sample. Binding of the nucleic acids to the solid phase preferably is performed under conditions having one or more, preferably at least two of the following characteristics:
 a) Binding is performed in the presence of at least one chaotropic agent,
 b) Binding is performed in the presence of at least one alcohol,
 c) Binding is performed in the presence of at least one detergent.

Respective binding conditions are well known in the prior art and thus, do not need a detailed description herein. The bound nucleic acids can be optionally washed and can be eluted if desired. Suitable washing and elution conditions are well known in the prior art and thus, do not need any further description.

The magnetic solid phase which was used for binding white blood cells can in certain embodiments also be used for isolating nucleic acids. This is for example feasible, if a magnetic solid phase is used for binding the blood cells, which is capable of binding nucleic acids under appropriate binding conditions. In this embodiment, the magnetic solid phase is preferably not separated, i.e. is not removed from the white blood cell fraction prior to isolating nucleic acids therefrom. Thus, the magnetic solid phase is in this embodiment present in the lysis mixture. Examples of respective magnetic solid phases include magnetic solid phases such as magnetic particles, comprising nucleic acid binding groups, such as for example anionic exchange groups. Accordingly, if a magnetic solid phase is used for binding the red and white blood cells which carries surface groups that are also capable of binding nucleic acids, nucleic acids released from white blood cells may either bind directly to the magnetic solid phase, e.g. if appropriate binding conditions are already provided in the lysis mixture, or suitable binding conditions may be established by the addition of appropriate binding agents. For example, if using anionic exchange groups as nucleic acid binding groups, the pH value of the lysis mixture can be lowered to establish a pH value which allows binding of the nucleic acids to the magnetic solid phase. The respectively bound nucleic acids can then be separated from the remaining lysis mixture by removing the magnetic solid phase. Suitable procedures for separating the magnetic solid phase were described above. After an optional washing step, the respectively isolated nucleic acids may optionally be eluted from the magnetic solid phase or may also be directly subjected while being bound to the magnetic solid phase to an analysis method, such as for example an amplification method, preferably a PCR reaction. Suitable conditions for washing and elution steps are known in the prior art and thus do not need any further description.

According to a further embodiment of the third aspect, the method for obtaining nucleic acids comprises
 (i) obtaining a blood fraction, namely white blood cells, according to the method of the second aspect of the present invention, wherein said white blood cell fraction may optionally comprise the magnetic solid phase that was used for binding the white blood cells,
 (ii) lysing white blood cells to release nucleic acids and
 (iii) optionally clearing the lysate, thereby providing a cleared lysate comprising the released nucleic acids, wherein said lysate clearing is preferably performed using the magnetic solid phase that was used to bind the white blood cells.

According to one embodiment, lysis in step (ii) is achieved by adding a lysis composition to the white blood cells. In said lysis step, the nucleic acids are released from the white blood cells. Preferably, lysis is assisted by heating. For example, the lysis mixture obtained by contacting the white blood cells and the magnetic solid phase with a lysis composition can be heated for at least one, preferably at least three, more preferably at least five minutes at a temperature of 80° C. or above, 85° C. or above, preferably 90° or above. Such a heating step results in a rapid lysis of the cells. A lysis composition which is suitable for this purpose and suitable lysis conditions are for at example described in WO 2010/003493, herein incorporated by reference. Preferably, the lysate is then cooled down to room temperature. The obtained lysate comprising the released nucleic acids can be used directly in analytical methods, such as e.g. in a PCR reaction. This is in particular the case if only small quantities of the lysate can be used, e.g. to qualitatively detect a certain nucleic acid that may be comprised in the lysate. According to a preferred embodiment, the lysate is cleared in order to remove contaminants such as precipitates or cell debris which may inhibit downstream reactions or assays such as in particular amplification methods if the lysate was used directly in larger quantities. Lysate clearing can be achieved by any suitable means such as e.g. by filtration. However, according to a preferred embodiment, the magnetic solid phase which was used for binding the white blood cells is used for lysate clearing. Preferably, the magnetic solid phase is provided by magnetic particles which preferably, carry carboxyl groups on their surface. In this embodiment, the magnetic solid phase is not separated from the white blood cells prior to lysis and accordingly, the magnetic solid phase is still comprised in the lysate. It was found that contaminants comprised in the lysate such as precipitates and cell debris bind to the surface of the magnetic solid phase and accordingly, can be easily separated from the remaining lysate by separating the magnetic solid phase, e.g. by performing a magnetic separation step. Thereby, the lysate is efficiently cleared. The released nucleic acids are basically "reversed purified" by removing at least a portion of contaminants and the respectively cleared lysate can be used directly in standard analytical methods, such as for example amplification methods or other detection methods. The advantage of clearing the lysate is that larger quantities can be used. This embodiment is particularly suitable if the magnetic solid phase carries carboxyl groups at its surface, however, also other functional groups mentioned above are suitable for this purpose.

The cleared lysate, may, however, also be subjected to a standard nucleic acid isolation procedure, wherein the nucleic acids comprised n the cleared lysate are further purified. Respective methods were described above and also belong to the prior art and accordingly, do need not be described in further detail herein.

According to a fourth aspect, the present invention pertains to the use of blood plasma and/or at least one blood fraction such as in particular a white blood cell fraction obtained according to the method of the first or second aspect of the present invention or nucleic acids obtained according to the third aspect of the present invention in an assay, preferably in an diagnostic assay.

The obtained nucleic acids may be further processed and/or analysed. For example they can be modified, contacted with at least one enzyme, amplified, reverse transcribed, cloned, sequenced, contacted with a probe and/or be detected. In particular the obtained nucleic acids such as for example cellular RNA or DNA obtained from the white blood cells and/or extracellular nucleic acids or viral nucleic acids obtained from blood plasma can be tested to identify the presence, absence or severity of a disease state. Therefore, the methods according to the present invention further contemplate a step of nucleic acid testing. Here, basically any standard testing method can be used. The analysis/further processing of the nucleic acids can be performed, e.g., using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here. According to one embodiment, the obtained nucleic acids are analysed to identify, detect, screen for, monitor or exclude a disease, an infection and/or at least one fetal characteristic.

The present methods as well as all three fractions obtained by the fractionation of whole blood according to the present method, i.e. blood plasma, lysate of red blood cells and white blood cells, may be used for the purpose of any analyses, in particular diagnostic analyses.

According to one embodiment, the fractions obtained by the present methods may be used in analytical methods. Thereby, for analyses by means of PCR, lyophilised PCR mastermixes, may directly be reconstituted with one of the fractions obtained by the present method, preferably with the obtained blood plasma. For optimal performance of PCR, the mastermixes should have a pH value of approximately 8 to 9 after reconstitution. A suitable pH value for PCR analysis may be achieved by the addition of sodium or potassium hydroxide, for example in form of small spheres, to the obtained blood plasma. Moreover, lyophilised PCR mastermixes may be applied, which comprise a higher amount of buffering substances. In order to inactivate proteins, which may be present in the blood plasma and which may inhibit PCR, the blood plasma may be lysed using a lysis buffers as disclosed in WO 2010/003493 A1, herein incorporated by reference.

Furthermore, as is shown by the examples, the plasma fraction obtained by the teachings of the present invention can be used in conjunction with an appropriate solvent, such as in particular water or an aqueous buffer, in order to reconstitute and thus rehydrate a dry composition comprising analytical reagents, such as in particular a dry composition comprising PCR reagents. Respective dry compositions are often used in order to simplify the procedure for the user. A respective dry reagent composition (respective compositions may be freeze dried) can be rehydrated by adding plasma and an appropriate solvent. Preferably, for a respective reconstitution, the amount of plasma that is obtained according to the teachings of the present invention is used in combination with an appropriate solvent in an amount of 75 vol % or less, preferably 60 vol % or less, more preferred 50 vol % or less.

The fractions obtained by the present method are also suitable for pathogen detection such as virus diagnostics, such as hepatitis A and/or hepatitis B diagnostics, for analyses of salt and sugar concentrations, for example sodium, potassium, calcium or glucose concentrations, or for analyses of marker proteins, for example albumine, ALT, ALP or AST. The fractions obtained by the present methods are also suitable for immunological diagnostics. Appropriate immunological tests are for example, without being limited thereto, ELISA, LateralFlow Assays, Luminex Assays, protein/antibody microassays, agglutination tests, flow through tests, line Blots and DipStick Tests.

In a preferred embodiment, a fraction obtained by the methods according to the present invention, in particular blood plasma, is used in automated applications such as diagnostic analyses or other analytical methods. The present method renders the centrifugation step, which is required in standard plasma preparation methods obsolete. The option to automate and integrate the present method into existing robotic systems for analysing clinical samples is an important advantage of the present invention. For example, the present method may be realised directly in a QIASYMPHONY® system (QIAGEN) or in a Point-of-Care-MDx device.

Furthermore, according to a fifth aspect, the present invention provides a kit that is suitable for performing the methods according to the first, second and/or third aspect of the present invention. Said kit comprises a magnetic solid phase, preferably magnetic particles for binding the red and white blood cells in method step b) described above. Preferably, the magnetic solid phase carries acidic surface groups, preferably carboxyl groups, amino groups or both. Examples of suitable and preferred magnetic solid phases as well as suitable and preferred surface groups and combinations thereof that are suitable for binding red and white blood cells under the conditions established in the sample mixture were described in detail above in conjunction with the methods according to the present invention. It is referred to the above disclosure, which also applies here.

Furthermore, the kit according to the present invention comprises an acidic red blood cell aggregation composition (A) which comprises at least one carboxylic acid and optionally, at least one osmotically active agent. As described above in conjunction with the methods according to the present invention, composition (A) is mixed with the whole blood sample, thereby preferably directly providing a sample mixture having a pH value that lies in a range selected from 2.5 to 5. Thereby, composition (A) is suitable to efficiently induce red blood cell aggregation and establishing the binding conditions for binding the red and white blood cells to the magnetic solid phase. In order to enable longer incubation periods of the whole blood sample with composition (A) and the magnetic solid phase, composition (A) preferably comprises an osmotically active agent as described above. Preferably, the red blood cell aggregation composition (A) is a solution. Preferably, the solution comprises citric acid as carboxylic acid. Preferably, citric acid is comprised in the red blood cell aggregation composition (A) in a concentration selected from the range of 30 mM to 80, preferably 30 mM to 60 mM. Alternatively or additionally, the red blood cell aggregation composition (A) may comprise glycine as at least one carboxylic acid. Preferably, glycine is comprised in the red blood cell aggregation composition (A) in a concentration selected from 25 mM to 750 mM, 30 mM to 500 mM, 30 mM to 250 mM, 30 mM to 150 mM, preferably 35 mM to 125 mM, more preferred 50 mM to 100 mM. As described above in conjunction with the methods according to the present invention, glycine does not provide a pH value in composition (A) that would be suitable to adjust upon mixture with the whole blood sample a pH value in the resulting sample mixture that lies within a range of 2.5 to 5. Therefore, when using glycine as carboxylic acid it is preferred that the pH value of the red blood cell aggregation composition (A) is adjusted to a pH value of 3.5 or less, 3.25 or less, 3 or less, 2.75 or less, 2.5 or less, 2 or less or 1.5 or less. This ensures that upon mixing with the whole blood sample a pH value is established in the sample mixture that lies in a pH range of 2.5 to 5 and preferably in the preferred pH ranges described above. For this purpose, composition (A) may comprise a further acid, preferably hydrochloric acid. The concentration of hydrochloric acid in the red blood cell aggregation solution (A) when using glycine as carboxylic acid is preferably at least 20 mM, preferably at least 25 mM, more preferred at least 30 mM. Other suitable examples of carboxylic acids and other suitable concentration ranges for the respective carboxylic acids, including citric acid and glycine, were described above in conjunction with the methods according to the present invention. It is referred to the above disclosure which also applies here and vice versa.

Additionally, as described above, it is preferred that the red blood cell aggregation composition (A) comprises an osmotically active agent as this provides more flexibility regarding the incubation period that is suitable for aggregating and binding the red blood cells to the magnetic solid phase without risking that substantial red blood cell lysis occurs. A longer possible incubation period renders the method less error-prone. Preferably, the red blood cell aggregation solution (A) comprises a carbohydrate or carbohydrate derivative as described above in conjunction with the method of the first aspect of the present invention as osmotically active agent in a concentration selected from 5% (w/v) to 50% (w/v), 7.5% (w/v) to 45% (w/v), 10% (w/v) to 40% (w/v), 10% (w/v) to 35% (w/v), 15% (w/v) to (30% (w/v), 20% (w/v) to 25% (w/v). As described above, the carbohydrate is preferably selected from the group consisting of monosaccharides, disaccharides, oligosaccharides, polysaccharides, non-reducing sugars and sugar alcohols and preferably is selected from trehalose, sucrose and glycerine. Suitable concentrations for the individual osmotically active agents are described above, it is referred to the above disclosure.

Optionally, the kit according to the present invention may comprise a red blood cell lysis composition (B). The red blood cell lysis composition (B) is preferably comprised in the kit if it is provided for the purpose of performing the method according to the second aspect of the present invention, as therein, the red blood cells are lysed. Details regarding the red blood cell lysis composition (B) that may be used for that purpose are described above, it is referred to the respective disclosure.

Additionally, the kit according to the present invention may comprise further reagents, such as for example one or more washing solutions and/or lysis compositions that are suitable for lysing white blood cells. Thus, optionally, the kit may comprise a white blood cell lysis buffer. Optionally, the kit may also comprise further reagents that are necessary for isolating nucleic acids from the obtained blood fraction. The kit may be advantageously used in one of the methods according to the present invention.

The term "solution" as used herein, in particular refers to a liquid composition, preferably an aqueous composition. It may be a homogenous mixture of only one phase but it is also within the scope of the present invention that a solution that is used according to the present invention comprises solid components such as e.g. precipitates.

According to one embodiment, subject matter described herein as comprising certain steps in the case of methods or as comprising certain ingredients in the case of compositions, such as composition (A) or other solutions and/or buffers refers to subject-matter consisting of the respective steps or ingredients.

Any acids described herein can be used in their free form or as salt. Both embodiments are encompassed by the term "acid". Preferably, the term acid refers to the free form.

It is preferred to select and combine preferred embodiments described herein and the specific subject-matter arising from a respective combination of preferred embodiments also belongs to the present disclosure.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

EXAMPLES

Example 1: Magnetic Separation of Blood Cells from Whole Blood

60 µl of EDTA stabilized whole blood were mixed in a 1.5 ml reaction vessel with 300 µl of composition (A) containing 50 mM citric acid and 0.85% (w/v) NaCl, briefly vortexted and incubated for 1 min at room temperature to induce red blood cell aggregation. Afterwards, 20 µl of a 5% (w/v) suspension of carboxylated magnetic beads (SERAMAG® DoubleSpeed Beads, Thermo Fisher) were added, the mixture was vortexed briefly and incubated for 30 sec at room temperature. For separating the magnetic beads with the bound red and white blood cells, the mixture was placed for 1 min in a magnetic separation devise. Finally, 150 µl of the separation supernatant were removed. The obtained blood plasma was clear and slightly yellow. To analyse, whether the supernatant comprised larger particles or unbound cells, the supernatant was centrifuged for 2 min at 6.000 rpm in a tabletop centrifuge. No pellet was formed at the bottom of the reaction vessel. This shows that the supernatant—blood plasma—was substantially cell-free. Thus, the method according to the present invention provides rapidly blood plasma of an acceptable quality.

Example 2: Determination of Preferred Citric Acid Concentration Ranges

Example 2 was performed as described in Example 1, wherein however, the whole blood samples were mixed with a composition (A) containing 30, 35, 40, 45, 50, 55, 60, 65 or 70 mM citric acid (see FIG. 1) and again 0.85% (w/v) NaCl.

Results:

Within a range of 30 to 60 mM citric acid, the separation of the blood cells provided the best results. The removed supernatant was clear and if at all only slightly reddish/orange (see FIG. 1) and no pellet was formed after centrifugation. Below said concentration range the RBCs were not successfully separated, as could be seen by the remaining turbidity of the obtained supernatant/blood plasma. Above said range of concentration the RBCs started to burst, as is indicated by the enhanced colouration of the supernatant. As described in the application above, it is possible to make pH value adaptions either in composition (A) or by adding an acid separately to the sample mixture in order to adjust a pH value in the sample mixture that provides blood plasma of the desired quality. Preferably, the pH value of the sample mixture lies in a pH range of 3 to 3.75.

Example 3: Aggregation of RBCs in the Presence of Magnetic Particles

The addition of magnetic particles to the aggregated RBCs is a further procedural step, that in order to provide a particularly rapid method, is preferably omitted. Example 3 investigates the possibility to add the magnetic particles before the aggregation of RBCs occurs. Example 3 was performed analogously to example 1. The magnetic particles, however, were either added together with composition (A) to the whole blood sample, or were added after the whole blood sample was contacted with composition (A) and accordingly, after the RBCs were already aggregated.

Results:

The 150 µl of supernatant obtained after 1 min in a magnetic separation device were clear and slightly yellowish. It made no difference whether the magnetic particles were added before or after aggregation of the RBCs. Thus, the presence of magnetic particles during the aggregation phase did not cause any problems. To the contrary, if the magnetic particles were already present during the RBC aggregation phase, the supernatant and accordingly the blood plasma contained significantly less suspended matter. Thus, respective suspended matter was removed more efficiently, if the magnetic particles were already present during RBC aggregation. Thus, adding the magnetic particles prior to aggregating the RBCs is advantageous as this allows to save time and handling steps and additionally, provides improved results. Preferably, the magnetic particles are included in the composition (A).

Figure 2:
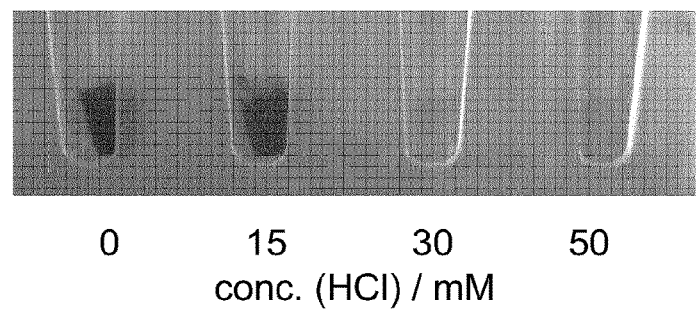
FIG. 2: Obtained blood plasma according to example 4 using glycine/HCl in composition (A). The figure shows the appearance of blood plasma depending on the used concentration (conc.) of glycine/HCl in composition (A).

Example 4: Magnetic Separation of Blood Cells Following Treatment with Glycine/HCl Carboxylated magnetic particles (SERAMAG®) were separated magnetically from 25 µl of a 5% suspension. The magnetic particles were resuspended in 300 µl of composition (A) containing 50 mM glycine, 0.85% (w/v) NaCl and rising concentrations of HCl (0, 15, 30, 50 mM) (see FIG. 2). The composition (A) comprising 50 mM glycine had a pH value of 5.8 without HCl and 2.4 after acidification with 30 mM HCl (at 22° C.). Subsequently, 60 µl of EDTA whole blood were added, the resulting mixture was vortexed briefly and incubated for 1 min at room temperature. For separating the magnetic beads, the mixture was placed for 1 min in a magnetic separation device. Finally, 150 µl of the supernatant i.e. the purified blood plasma were removed.

Results:

The separation was successful in the presence of 30 mM HCl or more. Here, the removed supernatant was clear and almost colourless (see FIG. 2). Thus, as is evident, the critical lowest concentration of HCl in the tested composition (A) was in the tested blood/composition (A) ratio between 15 mM and 30 mM. This example shows that it is important to achieve a specific pH value in the sample mixture comprising the whole blood sample and composition (A) comprising the carboxylic acid, here glycine. As is shown by example 4, an appropriate pH adjustment can be achieved by a composition (A) comprising glycine, if composition (A) is rendered sufficiently acidic that if mixed with the whole blood sample provides a sample mixture having a pH value in the desired pH range. However, as described above, it is also possible to adjust the pH value in the sample mixture, e.g. after the whole blood sample was contacted with composition (A).

Example 5: Effect of pH Value and Carboxylic Acid Comprised in Composition (A) on Separation of Blood Cells To investigate the effect of different acidities of composition (A) and the necessity to use a carboxylic acid for RBC aggregation, magnetic particles (SERAMAG®) were separated magnetically from 40 µl of a suspension and were resuspended with 400 µl of composition (A) containing 100 mM glycine, 100 mM NaCl, 0-60 mM HCl (see Tab. 1) and 20% (w/v) of trehalose, or for comparison with 400 µl of 20-60 mM HCl (in steps of 10 mM), respectively.

100 µl of an EDTA whole blood sample were added to the bead suspensions and mixed. All batches were incubated for 5 min at room temperature and the magnetic particles with the bound blood cells were then magnetically separated for 2 min. 350 µl of each resulting supernatant were transferred to a new vessel, a photo was taken (see FIG. 3) and the pH-value of each supernatant was measured with a pH-meter. The measured pH value of the supernatant basically corresponds to the pH value in the sample mixture.

Figure 3:
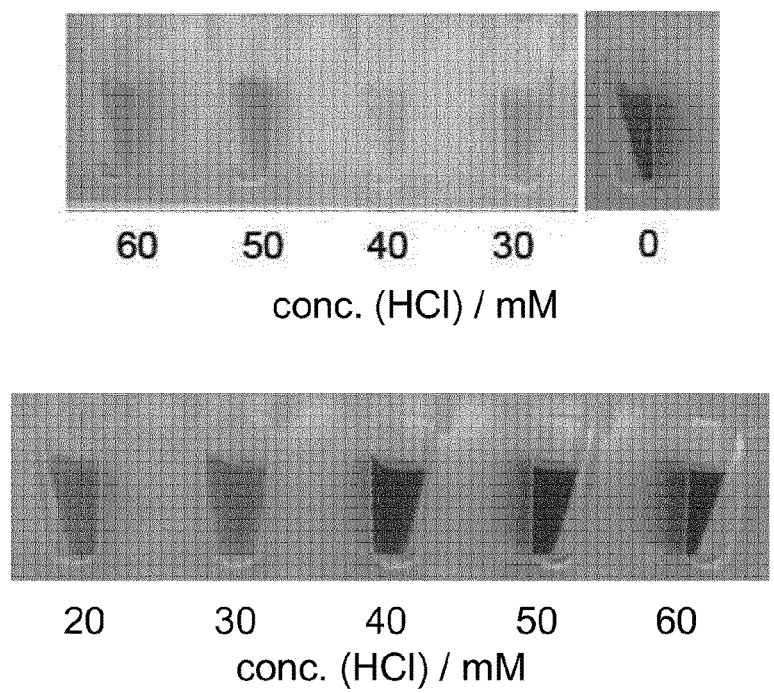
FIG. 3: Effect of pH value and carboxylic acid in composition (A) on separation. The figure shows the appearance of blood plasma depending on the used concentration (conc.) of HCl, both in the presence (top) and in the absence (bottom) of 100 mM glycine (see example 5).

Results:

Tab. 1 summarises the observations as presented in FIG. 3. The experiment shows that the experimental set-ups which use a composition (A) containing glycine and when mixed with whole blood provide a sample mixture having a pH value between 2.5 and 5, preferably 3 and 4 produce clear and (almost) colourless blood plasma. The test settings according to the present invention are marked bold. However, the test settings without glycine in composition (A) show that an acidic pH value alone (without the addition of a carboxylic acid—not according to the invention) was not sufficient for enabling a proper RBC separation, because despite of a suitable pH value in the sample mixture no colourless blood plasma could be obtained. Rather, the supernatant was red or brown which indicates a significant lysis of RBCs. Thus, the successful separation of blood cells depends on both, the pH value and the presence of a sufficient amount of carboxylic acid in the sample mixture.

TABLE 1

Results obtained in Example 5

| Composition (A) (content) | Turbidity | Colouration | pH value of the supernatant (=sample mixture) |
|---|---|---|---|
| 100 mM glycine + 60 mM HCl | Clear | only slightly brownish | 2.78 |
| 100 mM glycine + 50 mM HCl | Clear | only slightly brownish | 2.88 |
| 100 mM glycine + 40 mM HCl | Clear | almost colourless | 3.16 |
| 100 mM glycine + 30 mM HCl | Clear | almost colourless | 3.55 |
| 100 mM glycine | Turbid | Red | 7.05 |
| 20 mM HCl | Turbid | light red | 4.03 |
| 30 mM HCl | Clear | Brownish | 3.67 |
| 40 mM HCl | Clear | Brown | 2.78 |
| 50 mM HCl | Clear | dark brown | 2.89 |
| 60 mM HCl | Clear | dark brown | 2.55 |

Example 6: Incubation Periods

In order to find the period of time for optimal aggregation of the RBCs, an experiment corresponding to Example 1 was performed, wherein, however, the incubation time varied. The period of time for incubation with composition (A), i.e. for the aggregation of RBCs, was varied as follows: 15 sec, 30 sec, 1 min, 2 min, 3 min and 5 min (see FIG. 4).

Figure 4:
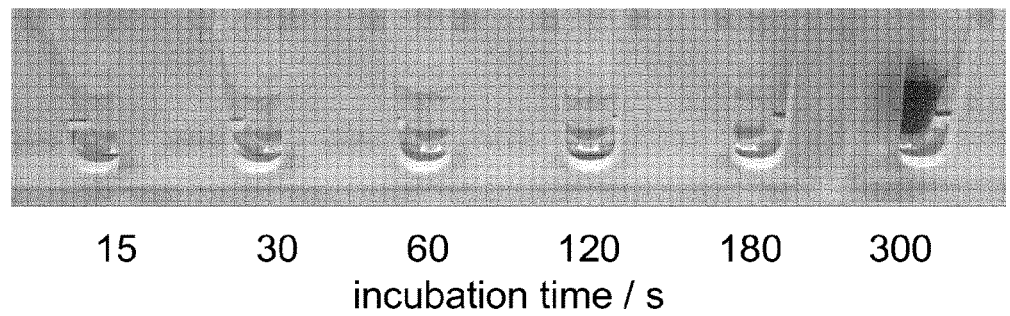
FIG. 4: Effect of the incubation period. The figure shows the appearance of blood plasma depending on the used incubation time with composition (A) (see example 6).

Results:

During an incubation period of 15 sec and to 3 min no difference in the quality of the separation and accordingly in the resulting blood plasma was observed. The obtained blood plasmas were clear and almost colourless (FIG. 4). However, an incubation time of 5 min resulted in a marked darkening of the supernatant, which indicates a massive lysis of the RBCs. Therefore, if not using an osmotically active agent, it is preferred to use an incubation time of 3 min or less.

Figure 5:
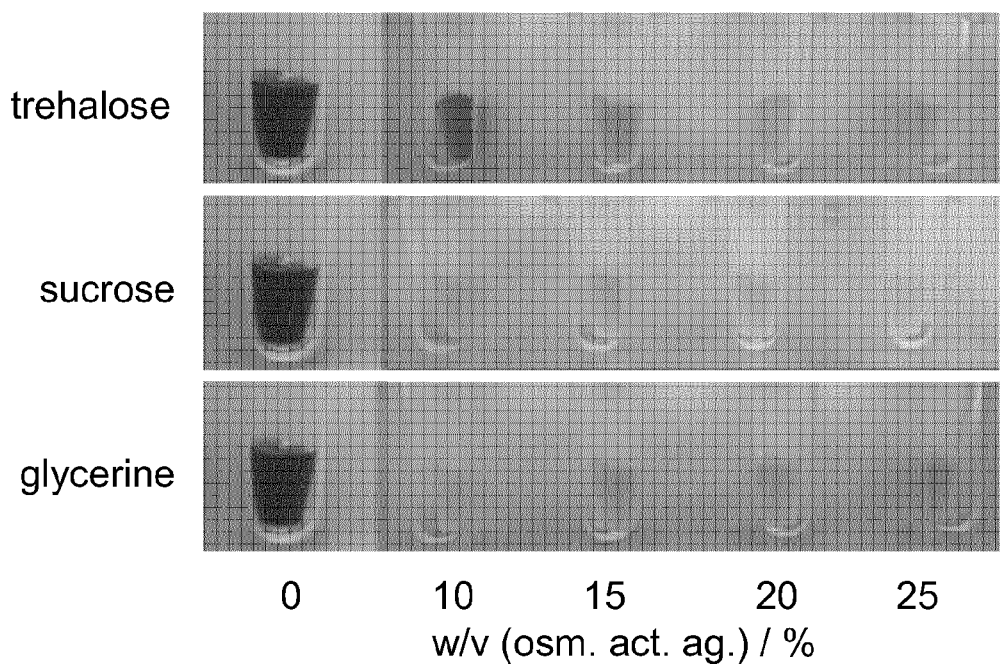
FIG. 5: Effect of osmotically active agents in composition (A). The figure shows the appearance of blood plasma depending on the used osmotically active agent (osm. act. ag; trehalose, sucrose, glycerine) in composition (A) and on the weight per mass percentage (w/v) of the osmotically active agent, after 6 min of incubation with composition (A) (see example 7).

Example 7: Effect of Osmotically Active Agents in Composition (A) on the Suitable Incubation Time Magnetic particles (SERAMAG®) were separated magnetically from 20 µl of a suspension and resuspended with 210 µl of composition (A) containing 100 mM glycine, 30 mM HCl, 33 mM NaCl and further comprising one of the additives trehalose, sucrose or glycerine each in concentrations of 10-25% (w/v) (in steps of 5%). To this magnetic particle suspension 50 µl of an EDTA stabilized whole blood sample were added and mixed. For comparison, 50 µl of EDTA stabilized whole blood were mixed with 210 µl of composition (A)/magnetic particles, however without an osmotically active agent as additive. All batches were incubated for 6 min at room temperature and were then separated magnetically for 2 min. 150 µl of each supernatant was transferred to a new vessel. FIG. 5 shows a photo of the resulting supernatants, i.e. blood plasmas.

Results:

As expected, the control batch without an osmotically active agent was coloured in dark red as expected, indicating significant lysis of RBCs (see FIG. 5). The batches "20-25% trehalose" were clear and almost colourless. The batches "10-25% sucrose" as well as "10-20% glycerine" were clear and colourless, too. Thus, a stabilising—i.e. RBC lysis avoiding—effect during the incubation with composition (A), i.e. during the aggregation of the RBCs, may be achieved by adding osmotically active substances like trehalose to the sample mixture. As discussed it is preferred to incorporate the respective agents in composition (A), in particular if longer incubation times are intended to be used.

Example 8: Fractionation of Whole Blood

The separation method according to the present invention is suitable for removing cellular constituents—i.e. red blood cells (RBCs) and white blood cells (WBCs)—from the whole blood sample. Furthermore, the separated cell fraction containing RBCs and WBCs may be fractionated further. Example 8 demonstrates that the technology of the present invention allows to obtain fractions of cell-free blood plasma, lysed RBCs and WBCs. For this purpose, magnetic particles (SERAMAG®) were separated magnetically from 20 µl of a suspension, the magnetic particle pellet was resuspended with 300 µl of composition (A) containing 50 mM glycine, 30 mM HCl and 100 mM NaCl. Then, 60 µl of EDTA stabilized whole blood (stored for two days) were added. The mixture was vortexed briefly, incubated for 3 min at room temperature and finally separated magnetically for 1 min.

Figure 6:
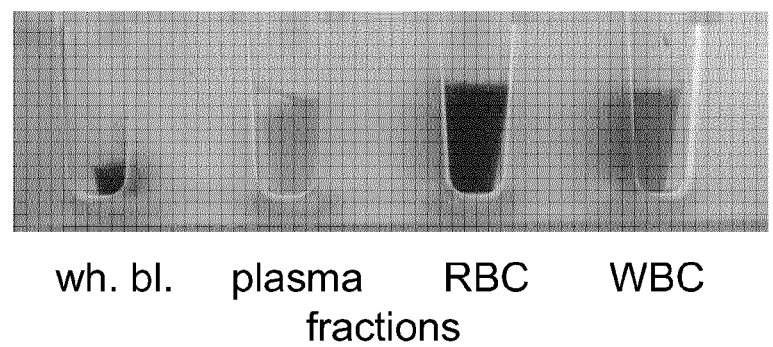
FIG. 6: Fractionation of whole blood into its constituents. The figure shows the appearance of the 3 different fractions obtained as well as of the initial whole blood sample (wh. bl.; 60 µl) (see example 8).

The cell-free supernatant was removed thereby rendering the fraction "blood plasma". The remaining blood cell containing material was resuspended with 300 µl RBC Lysis Solution (5'Prime). By this step, the RBCs that were bound to the magnetic particles and separated from the blood plasma fraction were lysed. WBCs are not lysed under these conditions. A further magnetic separation separated the magnetic particles with the still bound WBCs from the RBC lysate. The RBC lysate rendered the fraction "RBC lysed". After removing the RBC lysate, the WBCs which were still bound to the magnetic particles were washed twice with 1 ml of PBS and subsequently resuspended in 300 µl of PBS, thereby rendering the fraction "WBC washed". In FIG. 6 the starting material and all obtained fractions are shown.

The DNA from 60 µl of the initial whole blood sample as well as from the entire volume of each fraction was purified with the QIAAMP® DNA Mini Kit (QIAGEN) and eluted in 50 µl. 2 µl of each eluate were added to a 25 µl quantitative real time PCR (qPCR) reaction mixture (QUANTIFAST® Multiplex PCR Mastermix, Qiagen) and the DNA content was determined with a primer/probe mixture for the robust quantification of human DNA. The used sequences are disclosed in WO002012038503.

Figure 7:
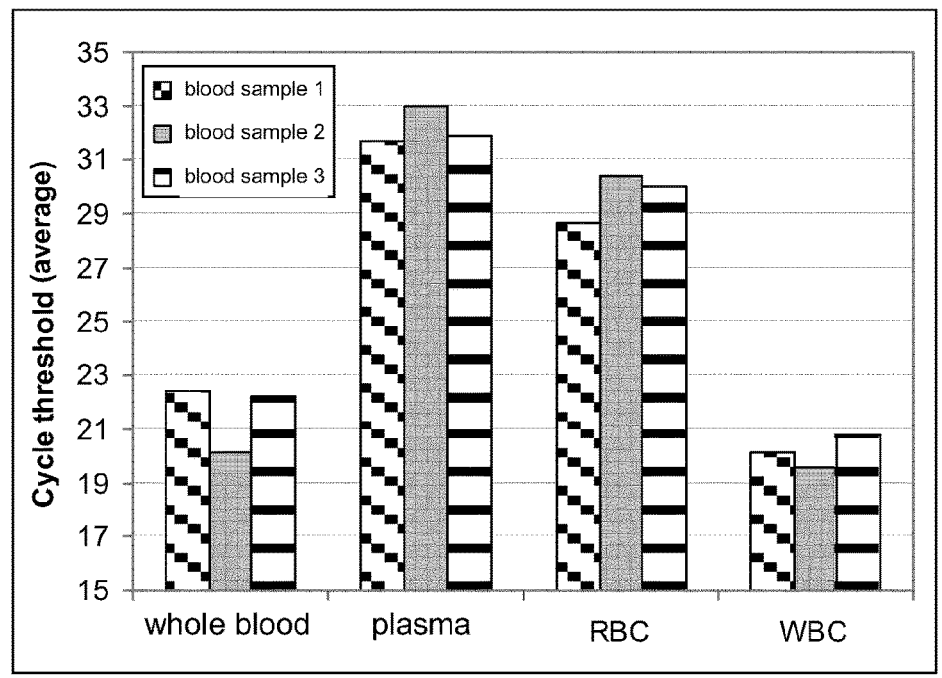
FIG. 7: Determination of human DNA in fractions of whole blood. The figure shows the average (n=2) ct-values (cycle threshold) of qPCR analysis for nucleic acids isolated from the fractions (plasma, RBC and WBC) obtained from 3 different whole blood samples as well as for nucleic acids isolated from the initial blood samples themselves (see example 8).

Results:

As is demonstrated in FIG. 7, the fractions "plasma" and "RBC" only contain approx. 0.1% of the DNA of the whole blood sample—a ct-difference of 10 corresponds to a difference in DNA concentration of approx. a factor 1000—which was almost completely recovered in the fraction "WBC". That the ct-values were even lower for "WBC" than for the original whole blood sample, may be explained by the lower content of PCR inhibitors in the "WBC fraction". In contrast to RBCs and blood plasma only WBCs contain chromosomal DNA. Thus, the result corresponds to the expected distribution of DNA over the different fractions and underlines the excellent quality of the fractionation of blood constituents according to the present invention.

Example 9: Suitability of Plasma Obtained by the Method According to the Present Invention for Virus Analytics In terms of clinical analyses, the following experiment demonstrates that the blood plasma obtained by the method according to the present invention may be used for the detection of viruses in blood. The sample material usually applied for the identification of e.g. hepatitis B or C viruses (HBV or HCV) is blood plasma that is obtained by centrifugation. Whole blood samples from three different donors were supplied with commercial HBV and HCV standards (Acrometrix). As described in the following, blood plasma was obtained from said whole blood samples conventionally and according to the present invention.

Analogously to the previous examples, the magnetic particles (SERAMAG®) were separated from 25 µl particle suspension and resuspended with 750 µl of composition (A) containing 50 mM glycine, 30 mM HCl and 100 mM NaCl. Then, 150 µl EDTA whole blood sample containing 2·10$^4$ IU of HBV standard as well as 5·10$^3$ IU of HCV standard (HBV and HCV QSSP Virus Standard, Acrometrix) were added. The sample was vortexed briefly and—after 3 min of incubation at room temperature—separated for 1 min in a magnetic separation device. In parallel, 200 µl of the same blood sample were centrifuged for 10 min at 2.500×g. 450 µl supernatant (containing 75 µl plasma) of the magnetically separated plasma solution and 75 µl of the centrifuged plasma, respectively, was subjected to nucleic acid isolation using the QIAAMP® MinElute Virus Kit (Qiagen). 6 µl of the internal control nucleic acids of the Artus® HBV RG and of the Artus® HCV RG PCR Kits (Qiagen) were added to the lysis buffer. The purified nucleic acids—DNA and RNA—were eluted with 60 µl elution buffer. 20 µl of each eluate were applied in 50 µl qPCR reactions (Artus® HBV and Artus® HCV RG Kit, Qiagen) and subjected to a PCR temperature profile following the manufacturer's instructions.

Figure 8:
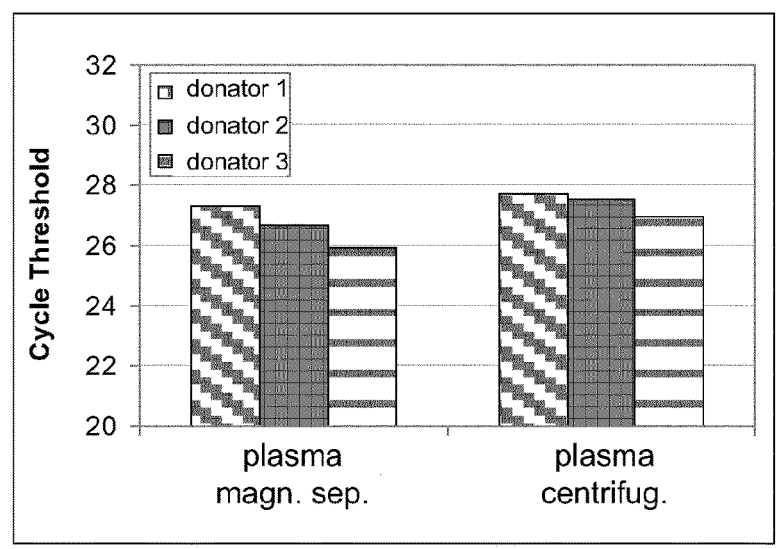
FIG. 8: Comparison of hepatitis B determination. The figure shows the ct-values (cycle threshold) for the qPCR determination of the hepatitis B virus nucleic acids isolated from blood plasma of 3 different donors. Blood plasma obtained magnetically (magn. sep.) and by centrifugation (centrifug.) is compared (see example 9).
Figure 9:
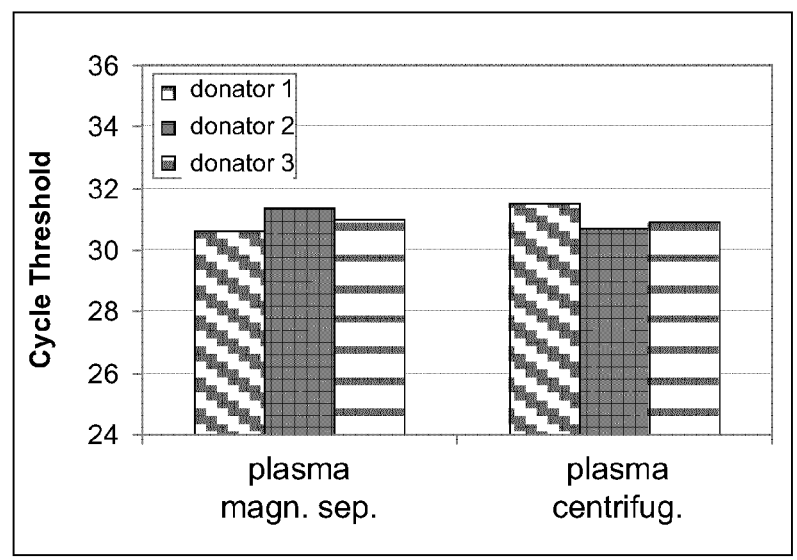
FIG. 9: Comparison of hepatitis C determination. The figure shows the ct-values (cycle threshold) for the qPCR determination of the hepatitis C virus nucleic acids isolated from blood plasma of 3 different donors. Blood plasma obtained magnetically (magn. sep.) and by centrifugation (centrifug.) is compared (see example 9).

Results:

The results are summarised in FIG. 8 and FIG. 9. The diagram in FIG. 8 displays the ct-values for the detection of HBV by qPCR. FIG. 9 shows the results of the HCV-specific qPCRs. The two figures clearly demonstrate, that both hepatitis viruses are equally detectable in the magnetically as well as in the conventionally produced blood plasma. In case of HBV, the ct-values are even lower for the magnetically produced blood plasma. Thus, compared to the blood plasma obtained by centrifugation, the blood plasma obtained by the present method is equally—or in case of HBV even more—suitable for virus diagnostics.

Example 10: Suitability of Plasma Obtained by the Method According to the Present Invention for Immunodiagnostics The use of plasma as sample material for immunodiagnostics is widespread. The following experiment demonstrates that the plasma obtained by the present method is compatible to immunoassays. As an example of such an immunoassay, a Chlamydia test of the company Kaul-o-test was performed.

Magnetic particles (SERAMAG®) were separated from 25 µl of particle suspension as described above. 750 µl of composition (A) containing 50 mM glycine, 30 mM HCl and 100 mM NaCl and subsequently 150 µl of EDTA stabilized whole blood were added. The mixture was vortexed and incubated for 1 min at room temperature. After magnetic separation, the supernatant i.e. the blood plasma, was removed and 150 µl of this plasma were supplied with 5 µl CT active culture (DSMZ 19131, aliquot stored at −80° C.). The mix was pipetted onto a Chlamydia Rapid Testing Cassette (Keul-o-test) and incubated for 3 min.

Figure 10:
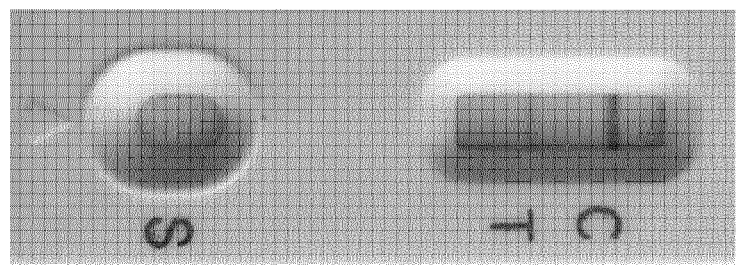
FIG. 10: Immunological determination of Chlamydia. The figure shows a Chlamydia Rapid Testing Cassette (Keul-o-test). "S" is the place of adding the sample. "C" is the control line and "T" is the test line indicating the presence of Chlamydia (see example 10).

Results:

The resulting colouration of the test line is shown in FIG. 10, indicating a positive Chlamydia test. Thus, the blood plasma obtained by the present method is suitable for immunological diagnostics as well.

Example 11: Separation by Means of Functionalised Magnetic Beads

Different magnetic particles comprising different surface groups were separated magnetically and resuspended with 200 µl of composition (A) containing 100 mM glycine, 100 mM NaCl, 30 mM HCl and 20% (w/v) trehalose. 50 µl of an EDTA stabilized whole blood sample were added and mixed with this suspension of beads. All batches were incubated for 5 min at room temperature and then separated magnetically for 2 min. 150 µl of each supernatant corresponding to blood plasma were transferred to a new vessel.

Results:

Tab. 2 summarises the observations. This example shows that besides carboxy functions also amino groups and combinations of different surface groups on the surface of the magnetic beads are suitable for the separation of the aggregated RBCs.

TABLE 2

Results obtained in example 11

| batch | surface of bead | turbidity | Colouration |
|---|---|---|---|
| 1. | carboxy (SERAMAG ®) | clear | Colourless |
| 2. | PEI/carboxy 5.1k | clear | Colourless |
| 3. | PEI/carboxy 2.1k(own synthesis) | clear | Colourless |
| 4. | carboxy (own synthesis) | clear | Colourless |

TABLE 2-continued

Results obtained in example 11

| batch | surface of bead | turbidity | Colouration |
|---|---|---|---|
| 5. | amino | clear | Colourless |
| 6. | AP/trimethylsilyl (TMS)/succinic acid | clear | Colourless |
| 7. | PEI/succinic acid | clear | Colourless |
| 8. | PEI/polyacrylic acid 2.1 | clear | Colourless |
| 9. | PEI/polyacrylic acid 5.1 | clear | Colourless |
| 10. | carboxy (own synthesis) | clear | Colourless |
| 11. | carboxy (own synthesis) | clear | Colourless |
| 12. | carboxy (own synthesis) | clear | Colourless |
| 13. | carboxy (own synthesis) | clear | Colourless |

Preferably, the pH value was between 3 and 4, more preferred 3 to 3.5.

Figure 11:
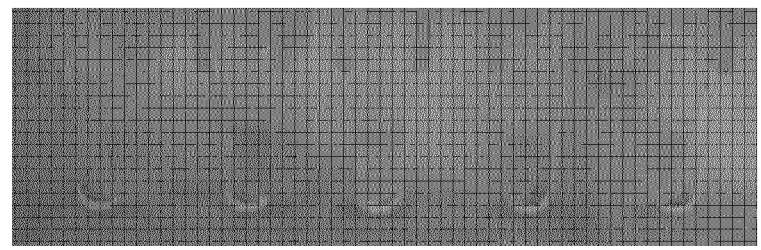
FIG. 11: Obtained blood plasma according to example 12. From left to right: glycine, malic acid, threonine, alanine, ascorbic acid.

Example 12: Magnetic Separation of Blood Cells Following Treatment with Different Carboxylate Acids Carboxylated magnetic particles (SERAMAG®) were separated magnetically from 25 µl of a 5% suspension. Magnetic particles were resuspended in 300 µl of composition (A) containing 50 mM of a carboxylic acid as specified in Tab. 3, 100 mM NaCl, 10% saccharose. Subsequently, 60 µl of EDTA stabilised whole blood was added and mixed. The resulting mixture was incubated for 3 minutes at room temperature and the magnetic particles were separated for 1 minute using a magnetic separation device. The resulting supernatant, i.e. the purified blood plasma was transferred into a new reaction vessel. FIG. 11 shows pictures of the resulting plasma.

TABLE 3

Results contained in example 12

| Carboxylic acid | pH-adjustment with | pH-value of composition (A) |
|---|---|---|
| 50 mM glycine | 30 mM HCl | 2.1 |
| 50 mM malic acid | No adjustment | 2.1 |
| 50 mM threonine | 30 mM HCl | 1.9 |
| 50 mM alanine | 45 mM HCl | 2.0 |
| 50 mM ascorbic acid | 15 mM HCL | 1.5 |

Results:

Tab. 3 summarises the observations as are also presented in FIG. 11. The data shows, that all listed carboxylic acids provide a separation result that is similar to glycine. This demonstrates that the method according to the present invention can be performed with various carboxylic acids as described herein.

Figure 12:
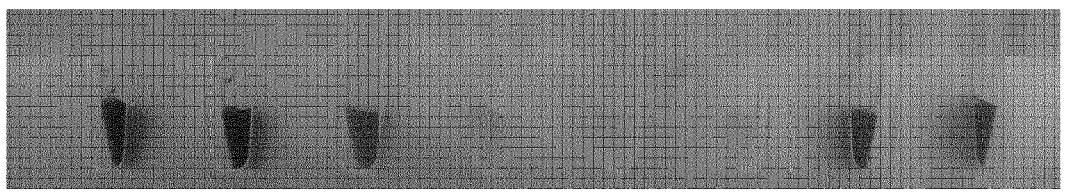
FIG. 12: Obtained blood plasma according to example 13. Far left: 1000 mM glycine/600 mM HCl; far right: 5 mM glycine/3 mM HCl.

Example 13: Effect of pH-Value and Concentration of Glycine Comprised in Composition (A) on the Separation of Blood Cells Carboxylated magnetic particles (SERAMAG®) were separated magnetically from 25 µl of a 5% suspension. The magnetic particles were resuspended in 300 µl of composition (A) containing difference amounts of glycine and HCl. The tested concentrations/dilutions are shown in Tab. 4. Subsequently 60 µl of EDTA stabilized whole blood was added and mixed. The resulting mixture was incubated for 3 minutes at room temperature. For separating the magnetic beads, the magnetic separation for 1 minute was performed. The supernatant, i.e. the purified blood plasma was transferred into a new reaction vessel and photographed. The results are shown in FIG. 12.

TABLE 4

Dilution series of a glycine/HCl buffer for producing plasma magnetically

| Glycine [mM] | HCl [mM] | pH value of the supernatant (=sample mixture) | Coloration of the supernatant |
|---|---|---|---|
| 1000 mM | 600 mM | 2.1 | Black |
| 500 mM | 300 mM | 2.2 | Black |
| 250 mM | 150 mM | 2.3 | Brownish |
| 100 mM | 60 mM | 2.65 | almost colorless |
| 50 mM | 30 mM | 3.45 | almost colorless |
| 25 mM | 15 mM | 4.8 | almost colorless |
| 10 mM | 6 mM | 6.4 | Red |
| 5 mM | 3 mM | 6.7 | Red |

Results:

The results of this experiment verify that the separation of intact erythrocytes is only possible within a very narrow pH range of approx. 2.5 to 5. Tab. 4 summarises the respective observations. If the pH value of the sample mixture (which correspond to the pH value of the supernatant) is below 2.5, this results in a lysis of the erythrocytes and the contained haemoglobin is denatured. This is visible due to the dark coloration of the supernatant. However, if the pH value of the sample mixture is above 5, no separation occurs. This can be seen due to the "blood red coloration" of the supernatant. This example confirms how difficult it is to bind red blood cells and further shows that specific binding conditions must be established in the sample mixture to allow binding of the red blood cells to the magnetic solid phase. As the present invention provides respective binding conditions, it is a significant contribution to the prior art.

Example 14: Magnetic Separation of Blood Cells from Whole Blood Using Different Buffer Concentrations This example is based on the previous examples. From the previous examples could be derived, that the successful magnetic plasma separation is only possible within a rather narrow pH range between 2.5 and 5, preferable 3 to 5. Furthermore, example 13 shows that the pH value of the sample mixture that is obtained when mixing composition (A) with whole blood corresponds predominantly to the pH value of composition (A), if composition (A) comprises at least 500 mM glycine.

Figure 13:
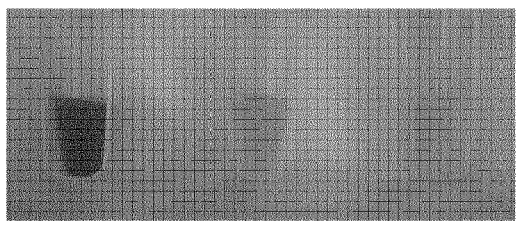
FIG. 13: Obtained blood plasma according to example 14. From left: 1000 mM, 500 mM, 50 mM glycine.

Carboxylated magnetic particles (SERAMAG®) were separated magnetically from 25 µl of a 5% suspension. The separated magnetic particles were resuspended in 300 µl of composition (A) containing glycine and HCl as shown in Tab. 5. Subsequently, 60 µl of EDTA stabilised whole blood was added to the particle suspension and mixed. After incubation for 3 minutes at room temperature the magnetic particles were separated for one minute. 150 µl supernatant was transferred into a new vessel and photographed. The results are shown in FIG. 13.

TABLE 5

Buffers used in example 14

| Glycine/ HCl [mM] | pH value of the composition (A) | Further additives | Supernatant |
|---|---|---|---|
| 1000 mM/50 mM | 3.6 | 10% saccharose, 100 mM NaCl | Red |
| 500 mM/25 mM | 3.6 | 10% saccharose, 100 mM NaCl | Slightly turbid and reddish |
| 50 mM/30 mM | 2.1 | No additives | clear, colorless |

Results:

Due to the previous examples it can be assumed that the pH value of the sample mixture lies in all tested versions of composition (A) in a range of 3 to 4. FIG. 13 shows that the separation worked best with the third composition (A). Furthermore, it is assumed that in the first tested embodiment (1000 mM glycine/50 mM HCl) the overall concentration of dissolved compounds in the sample mixture and thus the osmotic activity is too high, which results in a disintegration of the erythrocytes due to osmotic effects.

Example 15: Magnetic Blood Cell Separation Using Different Buffer Concentrations This example is also based on the previous observation. The previous examples have shown that the successful magnetic plasma separation is only possible within a pH range of 2.5 to 5, preferably 3 to 5. Furthermore, example 13 shows that the pH value of the blood/buffer mixture corresponds predominantly to the pH value of composition (A) if composition (A) comprises at least 500 mM glycine.

Carboxylated magnetic particles (SERAMAG®) were separated magnetically from 25 µl of a 5% suspension. The magnetic particles were resuspended in 300 µl of composition (A) as shown in Tab. 6. Subsequently, 60 µl of EDTA stabilised whole blood was added to the first three compositions, 30 µl EDTA stabilised blood was added to the fourth composition.

Figure 14:
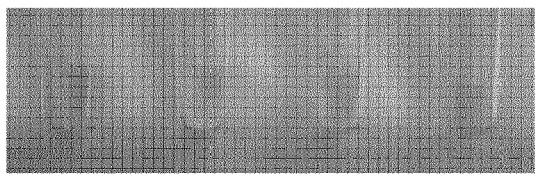
FIG. 14: Obtained blood plasma according to example 15. From left to right: compositions 1 to 4 according to table 6.

The results are shown in FIG. 14.

TABLE 6

Influence of the composition (A):blood mixing ratio

| Glycine/ HCl [mM] | Further additives | pH value of the sample mixture | Supernatant |
|---|---|---|---|
| 500 mM/25 mM | 10% saccharose, 100 mM NaCl | 4.2 | slightly turbid, yellowish |
| 500 mM/25 mM | no additives | 4.1 | clear, colorless |
| 50 mM/30 mM | no additives | 3.45 | clear, colorless |
| 50 mM/30 mM | no additives | 4.7 (only 30 µl blood) | clear, colorless |

Results:

The comparison between the first and second tested composition (A) confirms that if the concentration of the dissolved compounds in composition (A) and accordingly the osmotic activity in the sample mixture is too high, that the separation result is impaired. Thus, when using higher concentrations of carboxylic acids it is preferred not to add further additives such as salts that contribute to the osmotic activity; at least such additives should not be added in high concentrations. A comparison between the 3 and 4th tested composition (A) shows, that the pH value of the sample mixture resulting from contacting the whole blood sample with composition (A), depends when using a constant composition (A) strongly on the mixing ratio of blood to composition (A). If the pH value in the obtained sample mixture is not in the range of 2.5 to 5 after addition of composition (A), suitable pH adjustments of the sample mixture can be made as is also described in the general description.

Example 16: Use of Magnetically Purified Blood Plasma for Reconstituting Dry Reagent Compositions 25 µl carboxylated beads were mixed with 750 µl composition (A) (comprising 50 mM glycine, 30 mM HCl and 100 mM NaCl) and 150 µl EDTA stabilized blood was added and incubated for two minutes at room temperature. Afterwards, the magnetic beads with the bound cells were separated using a magnet and 500 µl supernatant (blood plasma) was transferred into a new vessel.

A lyophilised PCR reagent composition was prepared as follows. 12.5 µl QuantiFast Multiplex mastermix, 2 µl 1M Tris/HCl pH8.5 and 0.25 µl mecA-primers/probes were lyophilised in PCR reaction tubes. The respectively lyophilized PCR reagents were reconstituted and thus rehydrated with different liquids (25 µl in total) according to the following Tab. 7:

TABLE 7

Rehydration conditions

| Nr. | Rehydration with composition (A) (glycine buffer) | Rehydration with plasma | Water |
|---|---|---|---|
| 1-4 | | | 25 |
| 5-8 | 5 | | 20 |
| 9-12 | 10 | | 15 |
| 13-16 | 15 | | 10 |
| 17-20 | 20 | | 5 |
| 21-24 | 25 | | 0 |
| 25-28 | | 5 | 20 |
| 29-32 | | 10 | 15 |
| 33-36 | | 15 | 10 |
| 37-40 | | 20 | 5 |
| 41-44 | | 25 | 0 |
| 45-52 | Standards (fresh) $0/10/10^2/10^3$ cp | | |

To all samples 1-44 genomic DNA (MRSA, 1000 cp) was added as template. The PCR program was five minutes 95° C. and then 40 cycles of 10 sec 95° C., 30 sec 60° C.

The results are shown in the subsequent Tab. 8:

TABLE 8

PCR results

| | Ct | ΔCt |
|---|---|---|
| H2O | 27.34 | |
| Glycin_5 | 27.44 | 0.10 |
| Glycin_10 | 27.29 | −0.05 |
| Glycine_15 | 28.32 | 0.98 |
| Glycine_20 | 34.11 | 6.77 |
| Glycine_25 | 40 | 12.66 |
| Plasma_5 | 31.88 | 4.54 |
| Plasma_10 | 31.01 | 3.67 |
| Plasma_15 | 30.82 | 3.48 |
| Plasma_20 | 39.68 | 12.34 |
| Plasma_25 | 40 | 12.66 |

As can be seen from the results, up to 60 vol % plasma could be added to reconstitute the dried PCR reagents.

Therefore, the method is well suitable to be used for rehydration in combination with an appropriate solvent such as water or a buffer. Furthermore, the plasma can also be added directly to an amplification reaction such as a PCR reaction. The quality of the obtained plasma is sufficiently high in order to allow detecting comprised target nucleic acids, in particular a qualitative and also depending on the intended use a quantitative detection.

The invention claimed is:

1. A method for obtaining blood plasma from a whole blood sample comprising the following steps:
    a) contacting the whole blood sample with a composition (A) comprising at least one carboxylic acid and optionally contacting the whole blood sample with one or more further additives to produce a sample mixture, wherein the sample mixture has a pH value that lies in a range from 2.5 to 5, and wherein the pH value of the sample mixture is achieved by the addition of composition (A) alone, by the addition of one or more acidifying reagents, or by the addition of composition (A) and one or more acidifying reagents;
    b) binding red and white blood cells of the whole blood sample to a magnetic solid phase, wherein step a) and step b) can be performed sequentially or simultaneously; and
    c) separating the magnetic solid phase with the bound cells from the remaining sample thereby providing blood plasma.

2. The method of claim 1, further comprising the following steps:
    d) contacting the magnetic solid phase with the bound cells with a composition that lyses red blood cells but not white blood cells;
    e) separating the magnetic solid phase with the bound white blood cells from the lysate of red blood cells;
    f) optionally washing the white blood cells; and
    g) optionally eluting the white blood cells from the magnetic solid phase.

3. The method according to claim 1, wherein the addition of composition (A) and optionally further additives to the whole blood sample provides a sample mixture having a pH that lies in a range selected from 2.5 to 4.75, 2.5 to 4.5, 2.75 to 4.25, 3 to 4, and 3 to 3.75.

4. The method according to claim 1, wherein composition (A) comprises the carboxylic acid in a concentration that lies in the range selected from 20 mM to 1M, 25 mM to 500 mM, 30 mM to 250 mM, 30 mM to 150 mM, 30 mM to 100 mM, 50 mM to 100 mM, and 30 mM to 75 mM, or wherein the concentration of the at least one carboxylic acid in the sample mixture comprising the whole blood sample, composition (A) and optionally further additives lies in a range selected from 10 mM to 850 mM, 15 mM to 550 mM, 20 mM to 350 mM, 22.5 mM to 250 mM, 25 mM to 200 mM, 27.5 mM to 175 mM, 30 mM to 125 mM, 30 mM to 100 mM, 30 mM to 80 mM, 30 mM to 75 mM, and 30 mM to 50 mM.

5. The method according to claim 1, wherein the at least one carboxylic acid is selected from the following group:
    a) mono-, di- or tricarboxylic acids,
    b) citric acid, ascorbic acid, and malic acid,
    c) citric acid,
    d) a carboxylic acid carrying at least one additional functional group,
    e) amino acids and derivatives thereof,
    f) glycine, threonine and alanine, and
    g) glycine.

6. The method according to claim 1, having one or more of the following characteristics:
    a) the magnetic solid phase is added after step a);
    b) the magnetic solid phase is contacted with composition (A) or the whole blood sample prior to or at the same time when contacting the whole blood sample with composition (A); and/or
    c) the magnetic solid phase is comprised in composition (A) and wherein said composition (A) comprising the magnetic solid phase is contacted with the whole blood sample.

7. The method according to claim 1, wherein in step a) one or more further additives are added.

8. The method according to claim 7, having one or more of the following characteristics:
    a) as additive, at least one osmotically active agent is added in step a);
    b) as additive, at least one acidifying reagent is added in step a) to adjust the pH value of the sample mixture;
    c) as additive, at least one salt is added;
    d) as additive optionally a buffering compound is added; and/or
    e) the one or more additives that are added in step a) are comprised in composition (A).

9. The method according to claim 8, wherein the osmotically active agent of (a) is a carbohydrate and is comprised in the acidic composition (A) in a concentration selected from 5% (w/v) to 50% (w/v), 7.5% (w/v) to 45% (w/v), 10% (w/v) to 40% (w/v), 10% (w/v) to 35% (w/v), 15% (w/v) to (30% (w/v), and 20% (w/v) to 25% (w/v).

10. The method according to claim 1, wherein the magnetic solid phase has one or more of the following characteristics:
    a) it carries ionic groups on its surface;
    b) it carries acidic groups at its surface selected from carboxyl groups, phosphoric acid groups and sulphuric acid groups; and/or
    c) it carries amino groups.

11. The method according to claim 1, wherein magnetic particles are used as the magnetic solid phase.

12. The method according to claim 1, further comprising isolating nucleic acids from the obtained blood plasma.

13. The method of claim 1, wherein the method is used in an assay conducted on or applied to the blood plasma or a nucleic acid obtained therefrom.

14. The method according to claim 13, wherein the assay is a diagnostic assay.

15. The method according to claim 2, further comprising:
    (h) lysing the white blood cells to release nucleic acids, and
    (i) optionally clearing the lysate, thereby providing a cleared lysate comprising the released nucleic acids.

16. The method according to claim 2, further comprising isolating nucleic acids from the white blood cell fraction obtained from step e), f) or g) of claim 2.

17. The method according to claim 2, wherein the method is used in an assay conducted on or applied to the white blood cell fraction obtained from step e), f) or g) of claim 2, or on a nucleic acid obtained from the white blood cell fraction.

18. The method according to claim 17, wherein the assay is a diagnostic assay.

19. The method according to claim 1, wherein the method is used in an assay conducted on or applied to the blood plasma or the red and white blood cell fraction obtained from step c) of claim 1 or conducted on or applied to a nucleic acid obtained from the blood plasma or the red and white blood cell fraction.

20. The method according to claim 8,
wherein the at least one osmotically active agent of characteristic a) has one or more of the following characteristics:
i) it is uncharged;
ii) it stabilizes cells comprised in the sample by inducing cell shrinking;
iii) it is cell impermeable;
iv) it is water-soluble;
v) it is a hydroxylated organic compound;
vi) it is a polyol;
vii) it is a hydroxyl-carbonyl compound;
viii) it is a carbohydrate or carbohydrate derivative;
ix) it is selected from monosaccharides, disaccharides, oligosaccharides, polysaccharides, non-reducing sugars, and sugar alcohol; and/or
x) it is a carbohydrate or carbohydrate derivative selected from the group consisting of trehalose, sucrose and glycerine;
wherein the at least one acidifying reagent of characteristic b) is an acid; and/or
wherein the at least one salt of characteristic c) is at least one alkali metal salt.

21. The method of claim 20,
wherein the hydroxylate organic compound of v) of characteristic a) comprises at least 3 hydroxy groups, and/or
wherein the at least alkali metal salt of characteristic c) is NaCl or KCl.

* * * * *